US011963752B2

(12) United States Patent
Lyu et al.

(10) Patent No.: US 11,963,752 B2
(45) Date of Patent: Apr. 23, 2024

(54) IMAGING SYSTEMS AND METHODS

(71) Applicant: SHANGHAI UNITED IMAGING HEALTHCARE CO., LTD., Shanghai (CN)

(72) Inventors: Jingyuan Lyu, Houston, TX (US); Qi Liu, Houston, TX (US); Zhongqi Zhang, Shanghai (CN); Jian Xu, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 1084 days.

(21) Appl. No.: 16/798,265

(22) Filed: Feb. 21, 2020

(65) Prior Publication Data

US 2021/0259568 A1 Aug. 26, 2021

(51) Int. Cl.
*A61B 5/055* (2006.01)
*A61B 6/00* (2006.01)
(Continued)

(52) U.S. Cl.
CPC .......... *A61B 5/055* (2013.01); *G01R 33/4616* (2013.01); *G01R 33/4818* (2013.01);
(Continued)

(58) Field of Classification Search
CPC ............ G01R 33/4835; G01R 33/5616; G01R 33/5614; G01R 33/5617; G01R 33/5611; G01R 33/4818; G01R 33/54; G01R 33/5608; G01R 33/4616; G01R 33/561; G01R 33/56316; G01R 33/56563;
(Continued)

(56) References Cited

U.S. PATENT DOCUMENTS 8,036,730 B1 * 10/2011 Damadian ............ A61B 5/7425
324/307
10,436,871 B2   10/2019 Li et al.
(Continued)

FOREIGN PATENT DOCUMENTS

CN    109872376 A    6/2019
WO    2014162300 A1  10/2014

OTHER PUBLICATIONS

Bo Zhao et al., Image Reconstruction From Highly Undersampled (k, t)—Space Data With Joint Partial Separability and Sparsity Constraints, IEEE Transactions on Medical Imaging, 31(9): 1809-1820, 2012.

(Continued)

*Primary Examiner* — Joseph M Santos Rodriguez
*Assistant Examiner* — Amy Shafqat
(74) *Attorney, Agent, or Firm* — METIS IP LLC

(57) ABSTRACT

An imaging method may include obtaining imaging data associated with a region of interest (ROI) of an object. The imaging data may correspond to a plurality of time-series images of the ROI. The imaging method may also include determining, based on the imaging data, a data set including a spatial basis and one or more temporal bases. The spatial basis may include spatial information of the imaging data. The one or more temporal bases may include temporal information of the imaging data. The imaging method may also include storing, in a storage medium, the spatial basis and the one or more temporal bases.

20 Claims, 9 Drawing Sheets

(51) Int. Cl.
| | |
|---|---|
| *A61B 6/03* | (2006.01) |
| *G01R 33/24* | (2006.01) |
| *G01R 33/46* | (2006.01) |
| *G01R 33/48* | (2006.01) |
| *G01R 33/483* | (2006.01) |
| *G01R 33/561* | (2006.01) |
| *G01R 33/563* | (2006.01) |
| *G01R 33/565* | (2006.01) |
| *G06T 3/00* | (2006.01) |
| *G06T 7/00* | (2017.01) |
| *G06T 7/215* | (2017.01) |
| *G06T 7/262* | (2017.01) |
| *G06T 7/269* | (2017.01) |
| *G06T 9/00* | (2006.01) |
| *G06T 11/00* | (2006.01) |

(52) U.S. Cl.
CPC ..... *G01R 33/561* (2013.01); *G01R 33/56316* (2013.01); *G01R 33/56563* (2013.01); *G01R 33/5659* (2013.01); *G06T 7/0016* (2013.01); G06T 9/008 (2013.01); *G06T 11/003* (2013.01); *G06T 11/005* (2013.01); *G06T 11/008* (2013.01); *A61B 6/032* (2013.01); *A61B 6/5205* (2013.01); *G01R 33/243* (2013.01); *G01R 33/4833* (2013.01); *G01R 33/5611* (2013.01); *G01R 33/5617* (2013.01); *G01R 33/5618* (2013.01); *G01R 33/5619* (2013.01); *G01R 33/56341* (2013.01); *G06T 3/0087* (2013.01); *G06T 7/0012* (2013.01); *G06T 7/215* (2017.01); *G06T 7/262* (2017.01); *G06T 7/269* (2017.01); *G06T 2207/10072* (2013.01); *G06T 2207/10084* (2013.01); *G06T 2207/10088* (2013.01); *G06T 2207/10092* (2013.01); *G06T 2207/10096* (2013.01); *G06T 2207/10104* (2013.01); *G06T 2207/10108* (2013.01); *G06T 2207/10132* (2013.01); *G06T 2207/10136* (2013.01); *G06T 2207/20182* (2013.01); *G06T 2207/30004* (2013.01); *G06T 2207/30048* (2013.01); *G06T 2210/41* (2013.01); *G06T 2210/52* (2013.01); *G06T 2211/40* (2013.01); *G06T 2211/416* (2013.01)

(58) Field of Classification Search
CPC .............. G01R 33/5659; G01R 33/243; G01R 33/4833; G01R 33/5618; G01R 33/5619; G01R 33/56341; G01R 33/56308; G01R 33/546; G01R 33/5602; G01R 33/56325; A61B 5/055; A61B 6/032; A61B 6/5205; A61B 5/0035; A61B 5/0033; A61B 6/03; A61B 6/52; A61B 8/00; A61B 8/52; G06T 7/0016; G06T 9/008; G06T 11/003; G06T 11/005; G06T 11/008; G06T 3/0087; G06T 7/0012; G06T 7/215; G06T 7/262; G06T 7/269; G06T 2207/10072; G06T 2207/10084; G06T 2207/10088; G06T 2207/10092; G06T 2207/10096; G06T 2207/10104; G06T 2207/10108; G06T 2207/10132; G06T 2207/10136; G06T 2207/20182; G06T 2207/30004; G06T 2207/30048; G06T 2210/41; G06T 2210/52; G06T 2211/40; G06T 2211/416; G16H 30/20

See application file for complete search history.

(56) References Cited

U.S. PATENT DOCUMENTS

| | | |
|---|---|---|
| 2013/0182930 A1 | 7/2013 | Trzasko et al. |
| 2014/0177941 A1 | 6/2014 | Docherty et al. |
| 2015/0296214 A1 | 10/2015 | Mahfoodh et al. |
| 2016/0018499 A1 | 1/2016 | Bornert et al. |
| 2016/0202336 A1 | 7/2016 | Liang et al. |
| 2016/0291107 A1 | 10/2016 | Rosen et al. |
| 2017/0234951 A1 | 8/2017 | Zhao et al. |
| 2017/0325707 A1 | 11/2017 | Spottiswoode et al. |
| 2018/0172788 A1 | 6/2018 | Levine et al. |
| 2018/0306882 A1* | 10/2018 | Li ................ G06F 18/214 |
| 2019/0346523 A1 | 11/2019 | Li et al. |
| 2020/0049785 A1* | 2/2020 | Liu ................ A61B 5/055 |
| 2020/0088823 A1 | 3/2020 | Stehning et al. |

OTHER PUBLICATIONS

Anthony G. Christodoulou et al., Magnetic Resonance Multitasking For Motion-Resolved Quantitative Cardiovascular Imaging, Nature Biomedical Engineering, 2018, 12 pages.

Jaime L. Shaw et al., Free-Breathing, Non-ECG, Continuous Myocardial T1 Mapping With Cardiovascular Magnetic Resonance Multitasking, Magnetic Resonance In Medicine, 81:2450-2463, 2018.

Ni, Hongyan et al., Parameters Optimization of Data Acquisition Techniques in Diffusion Tensor Imaging, Journal of Tianjin University, 40(9): 1120-1127, 2007.

Wu, Shan, Sparse Tensor Based Magnetic Resonance Imaging Algorithm, China Excellent Master's Dissertation Full-text Database Information Technology Series, 2018, 80 Pages.

Ravishankar, Saiprasad et al., Image Reconstruction: From Sparsity to Data-Adaptive Methods and Machine Learning, Proceedings of the IEEE, 108(1): 1-24, 2020.

* cited by examiner

600

Obtaining magnetic resonance (MR) data associated with a region of interest (ROI) of an object, the MR data being acquired by scanning the ROI using an MRI scanner based on a plurality of parameters, the MR data corresponding to a plurality of time-series images of the ROI — 610

Determining, based on the MR data, a data set including a spatial basis and one or more temporal bases, the spatial basis including spatial information of the MR data, the one or more temporal bases including temporal information of the MR data — 620

Reconstructing at least a portion of the plurality of time-series images based on the data set — 630

Storing, in a storage medium, the reconstructed images and at least a portion of the data set — 640

- Obtaining, from a storage medium, a data set including a spatial basis and one or more temporal bases, the spatial basis and the one or more temporal bases corresponding to a plurality of time-series images of a region of interest (ROI) of an object — 910

- Receiving an instruction of reconstructing one or more target images of the plurality of time-series images — 920

- For each of the one or more target images, determining a temporal basis sub-set of each of the one or more temporal bases based on the instruction — 930

- Reconstructing the target image based on the data set and the one or more temporal basis sub-sets — 940

- Displaying the one or more target images — 950

- Storing at least one of the one or more target images in the storage medium — 960

FIG. 9

IMAGING SYSTEMS AND METHODS

TECHNICAL FIELD

The present disclosure generally relates to imaging, and in particular, to systems and methods for storage and display of images.

BACKGROUND

Imaging, such as dynamic medical imaging, may involve a large number of images. Merely by way of example, MRI real-time dynamic imaging, multi-contrast imaging, and parametric imaging refer to the continuous acquisition of multiple MRI images over a period of time, reflecting the movement of the measured object over time and/or the change in contrast over time. However, the MRI real-time dynamic imaging, multi-contrast imaging, and parametric imaging may involve a large number of images. For example, a heart 3D free breathing T1 quantitative dynamic contrast enhancement (DCE) application corresponding to 20 cardiac cycles, 88 saturation times, 12 slices, 75 heartbeats may involve 1,584,000 images. As still another example, a four-dimensional (4D) flow application corresponding to three-dimensional (3D) spatial dimension, a cardiac cycle dimension, and a flow coding direction dimension may involve more than 10,000 images. Storing, transmitting, and/or displaying such a large number of images in the form of, e.g., digital imaging and communications in medicine (DICOM), are resource-consuming, which increases the pressure on the medical system, e.g., the scanner and the picture archiving and communication system (PACS). Therefore, it is desirable to provide systems and/or methods for storage and/or displaying of medical images to solve the above problems.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

According to a first aspect of the present disclosure, an imaging system may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain imaging data associated with a region of interest (ROI) of an object. The imaging data may correspond to a plurality of time-series images of the ROI. The one or more processors may determine, based on the imaging data, a data set including a spatial basis and one or more temporal bases. The spatial basis may include spatial information of the imaging data. The one or more temporal bases may include temporal information of the imaging data. The one or more processors may store, in a storage medium, the spatial basis and the one or more temporal bases.

In some embodiments, the spatial basis and the one or more temporal bases may relate to a low-rank model that indicates a correlation between the plurality of time-series images.

In some embodiments, the spatial basis may include a spatial basis matrix and the one or more temporal bases may include a single temporal basis matrix. The spatial basis matrix in combination with the temporal basis matrix may represent a low-rank matrix corresponding to a collection of the plurality of time-series images. Elements in the spatial basis matrix and the temporal basis matrix may be fewer than elements in the low-rank matrix.

In some embodiments, the data set may further include a core tensor. The spatial basis may include a spatial basis matrix and the one or more temporal bases may include two or more temporal basis matrices. The spatial basis matrix in combination with the two or more temporal basis matrices and the core tensor may represent a low-rank multidimensional tensor corresponding to a collection of the plurality of time-series images. Elements in the core tensor, the spatial basis matrix, and the two or more temporal basis matrices may be fewer than elements in the low-rank multidimensional tensor.

In some embodiments, the low-rank multidimensional tensor may include a spatial dimension corresponding to the spatial basis matrix, and two or more time dimensions each of which corresponds to one of the two or more temporal basis matrices, respectively.

In some embodiments, the one or more processors may store the core tensor in the storage medium.

In some embodiments, the one or more processors may reconstruct at least a portion of the plurality of time-series images based on the data set. The one or more processors may store the reconstructed images in the storage medium.

In some embodiments, the one or more processors may transmit the reconstructed images to a user device to present the reconstructed images.

In some embodiments, the reconstructed images may include at least one set of images of the plurality of time-series images that indicate a variation of values of one of a plurality of parameters over time. The plurality of parameters may be configured to acquire the imaging data.

In some embodiments, the plurality of parameters may relate to at least one of cardiac motion, respiratory motion, or one or more imaging sequence parameters.

In some embodiments, the storage medium may include the at least one storage device or a picture archiving and communication system (PACS).

In some embodiments, the plurality of time-series images may include magnetic resonance (MR) images, computed tomography (CT) images, ultrasound images, or multi-modality images.

According to another aspect of the present disclosure, an imaging method may include one or more of the following operations. One or more processors may obtain imaging data associated with a region of interest (ROI) of an object. The imaging data may correspond to a plurality of time-series images of the ROI. The one or more processors may determine, based on the imaging data, a data set including a spatial basis and one or more temporal bases. The spatial basis may include spatial information of the imaging data. The one or more temporal bases may include temporal information of the imaging data. The one or more processors may store, in a storage medium, the spatial basis and the one or more temporal bases.

According to yet another aspect of the present disclosure, an imaging system may include a first input/output (I/O)

module configured to obtain imaging data associated with a region of interest (ROI) of an object. The imaging data may correspond to a plurality of time-series images of the ROI. The imaging system may also include a matrix determination module configured to determine, based on the imaging data, a data set including a spatial basis and one or more temporal bases. The spatial basis may include spatial information of the imaging data. The one or more temporal bases may include temporal information of the imaging data. The first I/O module may be further configured to store, in a storage medium, the spatial basis and the one or more temporal bases.

According to yet another aspect of the present disclosure, a non-transitory computer readable medium may comprise at least one set of instructions. The at least one set of instructions may be executed by one or more processors of a computer server. The one or more processors may obtain imaging data associated with a region of interest (ROI) of an object. The imaging data may correspond to a plurality of time-series images of the ROI. The one or more processors may determine, based on the imaging data, a data set including a spatial basis and one or more temporal bases. The spatial basis may include spatial information of the imaging data. The one or more temporal bases may include temporal information of the imaging data. The one or more processors may store, in a storage medium, the spatial basis and the one or more temporal bases.

According to yet another aspect of the present disclosure, an imaging system may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain, from a storage medium, a data set including a spatial basis and one or more temporal bases. The spatial basis and the one or more temporal bases may correspond to a plurality of time-series images of a region of interest (ROI) of an object. The spatial basis may include spatial information of the plurality of time-series images, and the one or more temporal bases may include temporal information of the plurality of time-series images. The one or more processors may receive an instruction of reconstructing one or more target images of the plurality of time-series images. The one or more processors may reconstruct the one or more target images based on the data set and the instruction. For each of the one or more target images, the one or more processors may determine a temporal basis sub-set of each of the one or more temporal bases based on the instruction. The one or more processors may reconstruct the target image based on the data set and the one or more temporal basis sub-sets. The one or more processors may display the one or more target images.

In some embodiments, to determine the temporal basis sub-set of each of the one or more temporal bases based on the instruction, the one or more processors may obtain, based on the instruction, a value of at least one of a plurality of parameters corresponding to the target image. The plurality of parameters may be configured to acquire imaging data of the ROI. The one or more processors may determine, based on the value of the at least one of the plurality of parameters, time information corresponding to the target image of the one or more temporal bases.

The one or more processors may determine, based on the time information, the temporal basis sub-set of each of the one or more temporal bases corresponding to the target image.

In some embodiments, the plurality of parameters may relate to at least one of cardiac motion, respiratory motion, or one or more imaging sequence parameters.

In some embodiments, the spatial basis and the one or more temporal bases may relate to a low-rank model that indicates a correlation between the plurality of time-series images.

In some embodiments, the spatial basis may include a spatial basis matrix and the one or more temporal bases may include a single temporal basis matrix. The spatial basis matrix in combination with the temporal basis matrix may represent a low-rank matrix corresponding to a collection of the plurality of time-series images. Elements in the spatial basis matrix and the temporal basis matrix may be fewer than elements in the low-rank matrix.

In some embodiments, to reconstruct the target image based on the data set and the one or more temporal basis sub-sets, the one or more processors may reconstruct the target image by determining a product of the spatial basis matrix and the temporal basis sub-set of the single temporal basis matrix.

In some embodiments, the data set may further include a core tensor. The spatial basis may include a spatial basis matrix and the one or more temporal bases may include two or more temporal basis matrices. The spatial basis matrix in combination with the two or more temporal basis matrices and the core tensor may represent a low-rank multidimensional tensor corresponding to a collection of the plurality of time-series images. Elements in the core tensor, the spatial basis matrix, and the two or more temporal basis matrices may be fewer than elements in the low-rank multidimensional tensor.

In some embodiments, the low-rank multidimensional tensor may include a spatial dimension corresponding to the spatial basis matrix, and two or more time dimensions each of which corresponds to one of the two or more temporal basis matrices, respectively.

In some embodiments, to reconstruct the target image based on the data set and the one or more temporal basis sub-sets, the one or more processors may reconstruct the target image by determining a product of the spatial basis matrix, the two or more temporal basis sub-sets of the two or more temporal basis matrices, and the core tensor.

In some embodiments, the one or more processors may store at least one of the one or more target images in the storage medium.

In some embodiments, the storage medium may include the storage device or a picture archiving and communication system (PACS).

In some embodiments, the plurality of time-series images may include magnetic resonance (MR) images, computed tomography (CT) images, ultrasound images, or multi-modality images.

According to yet another aspect of the present disclosure, an imaging method may include one or more of the following operations. One or more processors may obtain, from a storage medium, a data set including a spatial basis and one or more temporal bases. The spatial basis and the one or more temporal bases may correspond to a plurality of time-series images of a region of interest (ROI) of an object. The spatial basis may include spatial information of the plurality of time-series images, and the one or more temporal bases may include temporal information of the plurality of time-series images. The one or more processors may receive an instruction of reconstructing one or more target images of the plurality of time-series images. The one or more processors may reconstruct the one or more target images based on the data set and the instruction. For each of the one or more target images, the one or more processors may determine a temporal basis sub-set of each of the one or more temporal bases based on the instruction. The one or more processors may reconstruct the target image based on the data set and the one or more temporal basis sub-sets. The one or more processors may display the one or more target images.

According to yet another aspect of the present disclosure, an imaging system may include a second input/output (I/O) module configured to obtain, from a storage medium, a data set including a spatial basis and one or more temporal bases. The spatial basis and the one or more temporal bases may correspond to a plurality of time-series images of a region of interest (ROI) of an object. The spatial basis may include spatial information of the plurality of time-series images, and the one or more temporal bases may include temporal information of the plurality of time-series images. The second I/O module may be further configured to receive an instruction of reconstructing one or more target images of the plurality of time-series images. The imaging system may also include a second reconstruction module configured to reconstruct the one or more target images based on the data set and the instruction.

Each of the one or more target images may be reconstructed by determining a temporal basis sub-set of each of the one or more temporal bases based on the instruction, and reconstructing the target image based on the data set and the one or more temporal basis sub-sets. The second I/O module may be further configured to display the one or more target images.

According to yet another aspect of the present disclosure, a non-transitory computer readable medium may comprise at least one set of instructions. The at least one set of instructions may be executed by one or more processors of a computer server. The one or more processors may obtain, from a storage medium, a data set including a spatial basis and one or more temporal bases. The spatial basis and the one or more temporal bases may correspond to a plurality of time-series images of a region of interest (ROI) of an object. The spatial basis may include spatial information of the plurality of time-series images, and the one or more temporal bases may include temporal information of the plurality of time-series images. The one or more processors may receive an instruction of reconstructing one or more target images of the plurality of time-series images. The one or more processors may reconstruct the one or more target images based on the data set and the instruction. For each of the one or more target images, the one or more processors may determine a temporal basis sub-set of each of the one or more temporal bases based on the instruction. The one or more processors may reconstruct the target image based on the data set and the one or more temporal basis sub-sets. The one or more processors may display the one or more target images.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6 is a flowchart illustrating an exemplary process for MRI reconstruction according to some embodiments of the present disclosure;

FIG. 9 is a flowchart illustrating an exemplary process for MRI reconstruction according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different levels in ascending order. However, the terms may be displaced by another expression if they achieve the same purpose.

Figure 3:
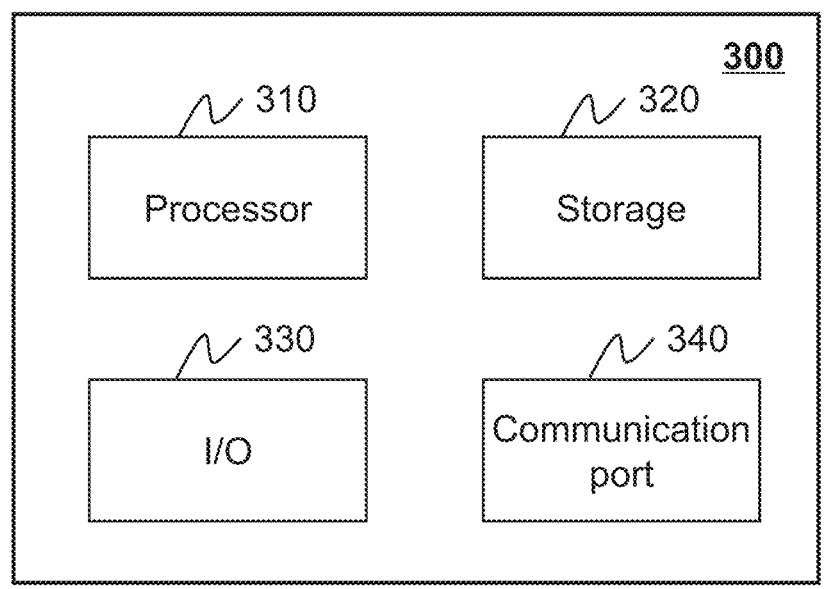
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a computed tomography (CT) system, a magnetic resonance imaging (MRI) system, a positron emission tomography (PET) system, an ultrasound system, or the like. Exemplary MRI systems may include a superconducting magnetic resonance imaging system, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, a computed tomography-positron emission tomography (CT-PET) system, etc. In some embodiments, the medical system may include a treatment system.

The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

An aspect of the present disclosure relates to systems and methods for storage and display of medical images. Taking systems and methods for storing and/or displaying MRI images as an example, magnetic resonance (MR) data corresponding to a plurality of time-series images of a region of interest (ROI) of an object may be obtained. In addition to spatial correlation of information represented in the plurality of time-series images, temporal correlation may also exist in the information represented in the plurality of time-series images. According to some embodiments, such spatial correlation and/or temporal correlation may be described by a low-rank model. During a process for image reconstruction based on the MR data, a spatial basis matrix including spatial information of the MR data and one or more temporal basis matrices including temporal information of the MR data may be determined based on the MR data and the low-rank model. Due to the low-rank feature of the temporal information in the form of the one or more temporal basis matrices and/or the spatial information in the form of the spatial basis matrix, the presentation of the MR data in the form of the spatial basis matrix and the one or more temporal basis matrices may have a smaller, even much smaller, data volume or file size than the plurality of time-series images. Accordingly, the spatial basis matrix and the one or more temporal basis matrices, instead of all of the plurality of time-series images, may be stored in, e.g., the picture archiving and communication system (PACS), which may reduce the occupied storage space.

If a user desires to view the plurality of time-series images in a user device, it is the spatial basis matrix and the one or more temporal basis matrices, rather than the plurality of time-series images themselves, that are transmitted from the PACS to the user device, which may reduce the amount of data to be transmitted, which in turn may alleviate the pressure on transmission bandwidth, reduce the transmission time, and/or reduce the chances of transmission error. With the spatial basis matrix and the one or more temporal basis matrices, fast reconstruction of any one of the plurality of time-series images may be achieved using the user device having an ordinary processing capacity.

It is understood that the disclosed methods and systems are described with reference to MRI images are provided for illustration purposes and not intended to be limiting. The disclosed methods and systems may be applied in other single or multi-modality imaging including, e.g., CT imaging, ultrasound imaging, MRI-CT, etc. In some embodiments, the methods and/or systems of storage and display of medical images in the present disclosure may be applied to scenarios of storage and/or display of medical images that are low-rank.

Figure 1:
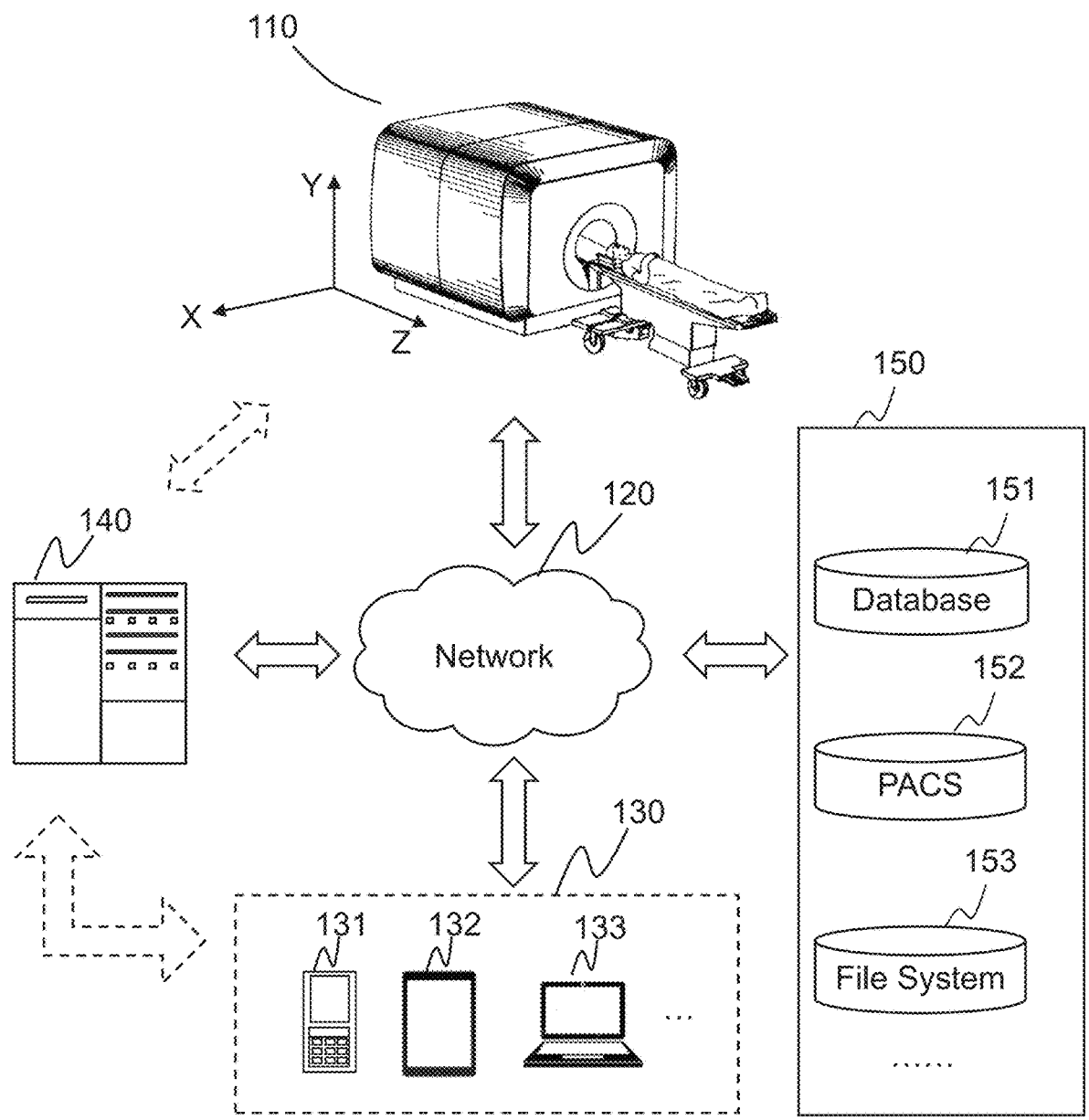
FIG. 1 is a schematic diagram illustrating an exemplary medical system according to some embodiments of the present disclosure.

FIG. 1 is a schematic diagram illustrating an exemplary medical system 100 according to some embodiments of the present disclosure. As illustrated, the medical system 100 may include a scanner 110, a network 120, a user device 130, a processing device 140, and a storage device 150. The components of the medical system 100 may be connected in one or more of various ways. Mere by way of example, as illustrated in FIG. 1, the scanner 110 may be connected to the processing device 140 through the network 120. As another example, the scanner 110 may be connected to the processing device 140 directly (as indicated by the bi-directional arrow in dotted lines linking the scanner 110 and the processing device 140). As a further example, the storage device 150 may be connected to the processing device 140 directly or through the network 120. As still a further example, a terminal device (e.g., 131, 132, 133, etc.) may be connected to the processing device 140 directly (as indicated by the bi-directional arrow in dotted lines linking the user device 130 and the processing device 140) or through the network 120.

The scanner 110 may scan an object located within its detection region and generate a plurality of imaging data relating to the object. In the present disclosure, "subject" and "object" are used interchangeably. Mere byway of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

In some embodiments, the scanner 110 may include an MRI scanner, a CT scanner, a PET scanner, an ultrasound scanner, a multi-modality device, etc. Exemplary multi-modality device may include an MRI-CT device, a PET-MRI device, a PET-CT device, etc. In the present disclosure, the X axis, the Y axis, and the Z axis shown in FIG. 1 may form an orthogonal coordinate system. The X axis and the Z axis shown in FIG. 1 may be horizontal, and the Y axis may be vertical. As illustrated, the positive X direction along the X axis may be from the right side to the left side of the scanner 110 seen from the direction facing the front of the scanner 110; the positive Y direction along the Y axis shown in FIG. 1 may be from the lower part to the upper part of the scanner 110; the positive Z direction along the Z axis shown in FIG. 1 may refer to a direction in which the object is moved out of the scanning channel (or referred to as the bore) of the scanner 110. More description of the scanner 110 may be found elsewhere in the present disclosure. See, e.g., FIG. 2 and the description thereof.

The network 120 may include any suitable network that can facilitate the exchange of information and/or data for the medical system 100. In some embodiments, one or more components of the medical system 100 (e.g., the scanner 110, the user device 130, the processing device 140, or the storage device 150) may communicate information and/or data with one or more other components of the medical system 100 via the network 120. For example, the processing device 140 may obtain imaging data (e.g., magnetic resonance (MR) data) from the scanner 110 via the network 120. As another example, the user device 130 may obtain a spatial basis matrix and one or more temporal basis matrices corresponding to the imaging data from the storage device 150 and/or the processing device 140. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a Zig-Bee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The user device 130 may include a mobile device 131, a tablet computer 132, a laptop computer 133, a desktop computer (not shown), a workstation (not shown), or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the user device 130 may remotely operate the scanner 110 and/or the processing device 140. In some embodiments, the user device 130 may operate the scanner 110 and/or the processing device 140 via a wireless connection. In some embodiments, the user device 130 may receive information and/or instructions inputted by a user, and send the received information and/or instructions to the scanner 110 or to the processing device 140 via the network 120. For example, a user (e.g., a doctor, a technician, or an engineer, etc.) of the medical system 100 may set a scan protocol though the user device 130. The user device 130 may send the scan protocol to the processing device 140 to direct the processing device 140 to control the scanner 110 (e.g., the MRI scanner) to operate according to the scan protocol. In some embodiments, the user device 130 may receive data and/or information from the processing device 140 and/or the storage device 150. For example, the user device 130 may obtain a spatial basis matrix and one or more temporal basis matrices from the processing device 140 and/or the storage device 150. As another example, the user device 130 may obtain one or more images from the processing device 140 and/or the storage device 150.

The processing device 140 may process data and/or information obtained from the scanner 110, the user device 130, and/or the storage device 150. For example, the processing device 140 may obtain imaging data (e.g., MR data) from the scanner 110 and determine a spatial basis matrix and one or more temporal basis matrices based on the imaging data. As another example, the processing device 140 may receive one or more instructions from the user device 130 and control the scanner 110 to operate according to the one or more instructions. In some embodiments, the processing device 140 may be a single server, or a server group. The server group may be centralized or distributed. In some embodiments, the processing device 140 may be local or remote. For example, the processing device 140 may access information and/or data stored in or acquired by the scanner 110, the user device 130, and/or the storage device 150 via the network 120. As another example, the processing device 140 may be directly connected to the scanner 110 (as illustrated by the bidirectional arrow in dashed lines connecting the processing device 140 and the scanner 110 in FIG. 1), the user device 130 (as illustrated by the bidirectional arrow in dashed lines connecting the processing device 140 and the user device 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the processing device 140 may be implemented on a computing device 300 having one or more components illustrated in FIG. 3 in the present disclosure.

The storage device 150 may store data and/or instructions. In some embodiments, the storage device 150 may include a database 151, a picture archiving and communication system (PACS) 152, a file system 153, or the like, or any combination thereof. In some embodiments, the storage device 150 may store data obtained from the scanner 110, the user device 130 and/or the processing device 140. For example, the storage device 150 may store imaging data (e.g., MR data) acquired by the scanner 110. As another example, the storage device 150 may store medical images (e.g., MRI images) generated by the processing device 140 and/or the user device 130. As a further example, the storage device 150 may store a spatial basis matrix and one or more temporal basis matrices. As a further example, the storage device 150 may store electronic medical records of patients. As a further example, the storage device 150 may store preset scan parameters (e.g., preset scan protocols) of the medical system 100. In some embodiments, the storage device 150 may store data and/or instructions that the processing device 140 may execute or use to perform exemplary methods described in the present disclosure. For example, the storage device 150 may store instructions that the processing device 140 may execute to determine a spatial basis matrix and one or more temporal basis matrices based on the imaging data. As another example, the storage device 150 may store instructions that the processing device 140 and/or the user device 130 may execute to generate one or more images based on the spatial basis matrix and the one or more temporal basis matrices. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the medical system 100 (e.g., the scanner 110, the processing device 140, the user device 130, etc.). One or more components of the medical system 100 may access the data or instructions stored in the storage device 150 via the network 120. In some embodiments, the storage device 150 may be directly connected to or communicate with one or more components of the medical system 100 (e.g., the scanner 110, the processing device 140, the user device 130, etc.). In some embodiments, the storage device 150 may be part of the processing device 140.

In some embodiments, the medical system 100 may further include one or more power supplies (not shown in FIG. 1) connected to one or more components of the medical system 100 (e.g., the scanner 110, the processing device 140, the user device 130, the storage device 150, etc.).

For brevity, the description of the methods and/or systems of storage and display of medical images may take MRI as an example. For example, the description below of the scanner 110 may be provided with reference to an MRI scanner as an example. As another example, the description below of the methods and/or systems of storage and display of medical images may be provided with reference to MR images as an example. It should be noted that the methods and/or systems of storage and display of MR images described below are merely some examples or implementations, and not intended to be limiting. For persons having ordinary skills in the art, the methods and/or systems of storage and display of MR images in the present disclosure may be applied to other similar single or multi-modality imaging including, such as, e.g., CT imaging, ultrasound imaging, MRI-CT, etc. In some embodiments, the methods and/or systems of storage and display of medical images in the present disclosure may be applied to scenarios of storage and/or display of medical images that are low-rank.

Figure 2:
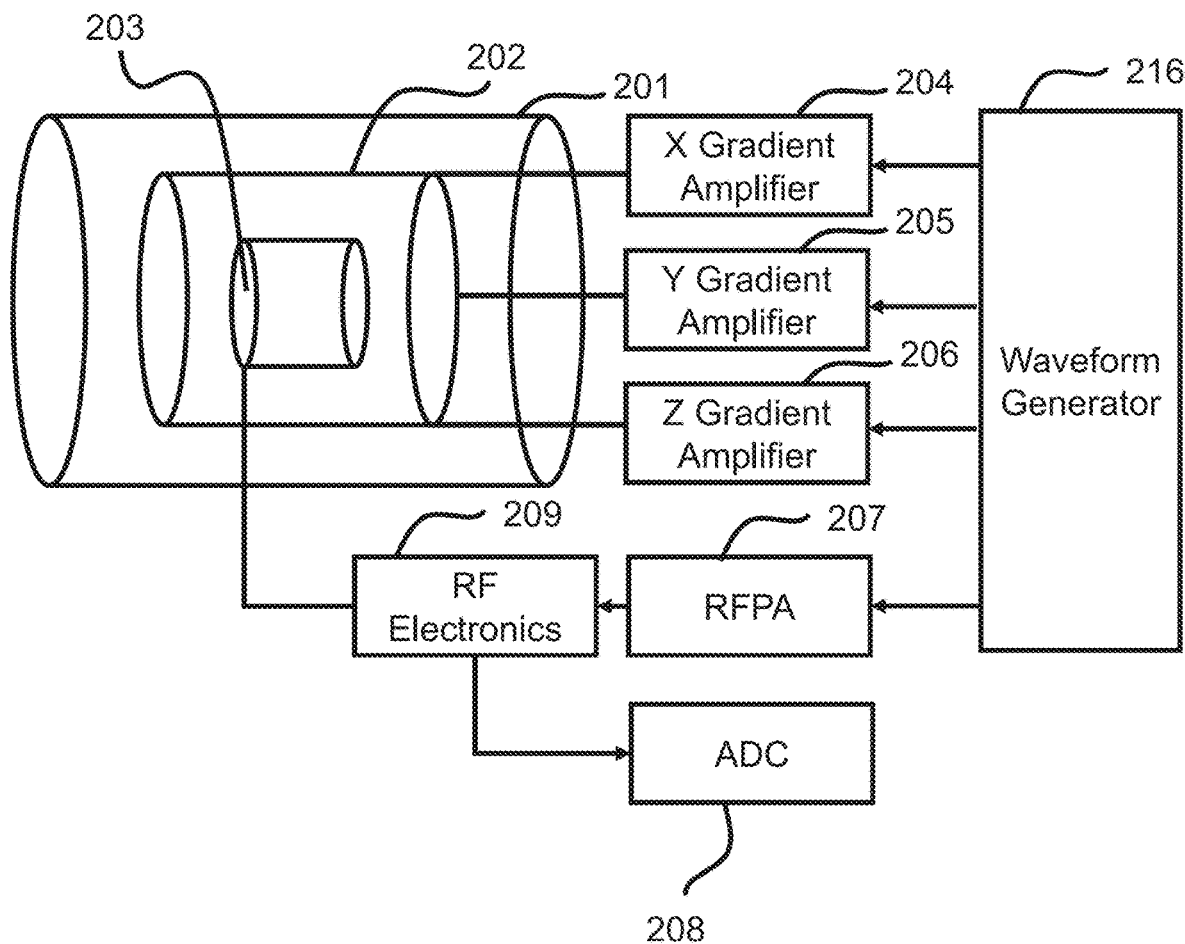
FIG. 2 is a schematic diagram illustrating an exemplary MRI scanner according to some embodiments of the present disclosure.

FIG. 2 is a schematic diagram illustrating an exemplary MRI scanner according to some embodiments of the present disclosure. As illustrated, the main magnet 201 may generate a first magnetic field (or referred to as a main magnetic field) that may be applied to an object (also referred to as a subject) exposed inside the field. The main magnet 201 may include a resistive magnet or a superconductive magnet that both need a power supply (not shown) for operation. Alternatively, the main magnet 201 may include a permanent magnet. The main magnet 201 may include a bore that the object is placed within. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of an object may vary as a function of their positions inside the gradient field, thereby encoding spatial information into MR signals generated by the region of the object being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate MR signals related to the region of the object being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting MR signals (e.g., echoes). After excitation, the MR signals generated by the object may be sensed by the RF coils 203. The receive amplifier then may receive the sensed MR signals from the RF coils 203, amplify the sensed MR signals, and provide the amplified MR signals to the ADC 208. The ADC 208 may transform the MR signals from analog signals to digital signals. The digital MR signals then may be sent to the processing device 140 for sampling.

In some embodiments, the gradient coils 202 and the RF coils 203 may be circumferentially positioned with respect to the object. It is understood by those skilled in the art that the main magnet 201, the gradient coils 202, and the RF coils 203 may be situated in a variety of configurations around the object.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the scanner 110 may further include an object positioning system (not shown). The object positioning system may include an object cradle and a transport device. The object may be placed on the object cradle and be positioned by the transport device within the bore of the main magnet 201.

MRI systems (e.g., the medical system 100 in the present disclosure) may be commonly used to obtain an interior image from a patient for a particular region of interest that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an MR signal. The MR signal is received and processed to form an MR image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the x, y, and z directions, having a particular timing, frequency, and phase, may be superimposed on the uniform magnetic field such that the RF excitation signal excites the H atoms in a desired slice of the patient's body, and unique phase and frequency information is encoded in the MR signal depending on the location of the H atoms in the "image slice."

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, saturation recovery sequences, or the like, or any combination thereof. For instance, the spin echo sequences may include fast spin echo (FSE), turbo spin echo (TSE), rapid acquisition with relaxation enhancement (RARE), half-Fourier acquisition single-shot turbo spin-echo (HASTE), turbo gradient spin echo (TGSE), or the like, or any combination thereof. The protocol may also include information regarding image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

For each MRI scan, the resulting MR signals (also referred to as MR data) may be digitized and processed to reconstruct an image in accordance with the MRI imaging protocol that is used.

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 310 may determine a spatial basis matrix and one or more temporal basis matrices corresponding to MR data. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be noted that the computing device 300 in the present disclosure may also include multiple processors, and thus operations of a method that are performed by one processor as described in the present disclosure may also be jointly or separately performed by the multiple processors. For example, if in the present disclosure the processor of the computing device 300 executes both operations A and B, it should be understood that operations A and step B may also be performed by two different processors jointly or separately in the computing device 300 (e.g., a first processor executes operation A and a second processor executes operation B, or the first and second processors jointly execute operations A and B).

Merely by way example, the processor 310 may receive instructions to follow an MRI scan protocol for imaging/scanning the object. For example, the processor 310 may instruct the object positioning system of the scanner 110 to move the object to a proper position within the bore of the main magnet 201. As another example, the processor 310 may also provide certain control signals to control the main magnet 201 to generate a main magnet field with a specific strength.

The processor 310 may receive control signals to set the shape, amplitude, and/or timing of the gradient waveforms and/or the RF waveforms, and send the set parameters to the waveform generator 216 to instruct the waveform generator 216 to generate a particular gradient waveform sequence and pulse sequence that are to be applied to the gradient coils 202 and the RF coils 203 through the amplifiers 204-207, respectively.

The processor 310 may also sample data (e.g., echoes) from the RF coils 203 based on one or more sampling parameters including, e.g., timing information (e.g., the length of data acquisition), the type of k-space data acquisition (e.g., undersampling, oversampling, etc.), sampling trajectory (e.g., Cartesian trajectory, non-Cartesian trajectory such as spiral trajectory, radial trajectory), or the like, or a combination thereof. In some embodiments, the timing information may be input by a user (e.g., an operator) or autonomously determined by the medical system 100 based on one or more other parameters (e.g., clinical needs) of an imaging process. The timing information may correspond to the type of the gradient and RF waveforms that are sent to the gradient coils 202 and the RF coils 203, respectively, so that the MR signals are correctly sampled. The processor 310 may also generate an MR image by reconstructing the sampled data.

The storage 320 may store data/information obtained from the scanner 110, the user device 130, the storage device 150, or any other component of the medical system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 140 for determining a spatial basis matrix and one or more temporal basis matrices based on MR data. In some embodiments, the storage 320 may store reconstructed MRI images and/or the spatial basis matrix and the one or more temporal basis matrices.

The I/O 330 may input or output signals, data, or information. In some embodiments, the I/O 330 may enable user interaction with the processing device 140. In some embodiments, the I/O 330 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the scanner 110, the user device 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
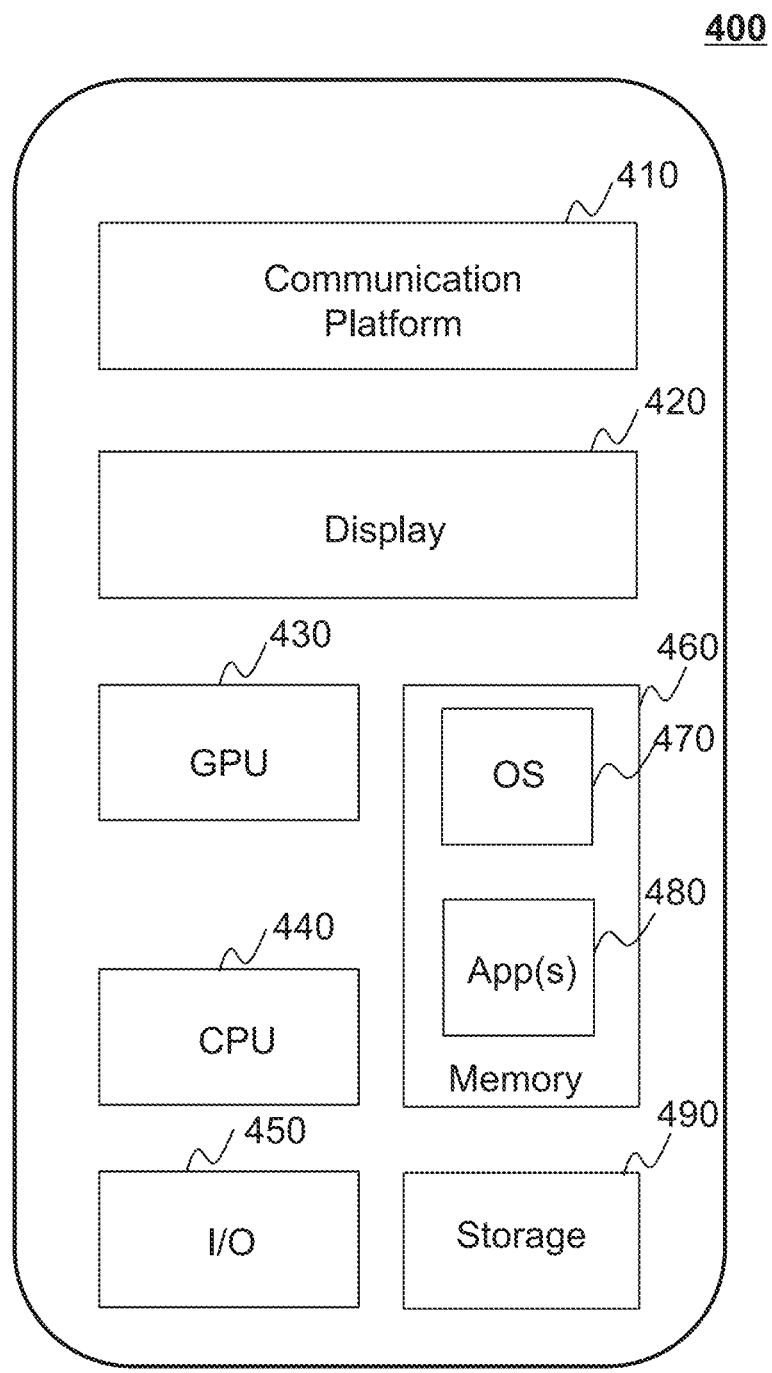
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the user device 130 may be implemented according to some embodiments of the present disclosure. As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the medical system 100 via the network 120. Merely byway of example, a user (e.g., a doctor, a technician, an engineer, an operator, etc.) of the medical system 100 may input data related to an object (e.g., a patient) that is being/to be imaged/scanned through the I/O 450. The data related to the object may include identification information (e.g., the name, age, gender, medical history, contact information, physical examination result, etc.) and/or the test information including the nature of the MRI scan that must be performed. The user may also input parameters needed for the operation of the scanner 110, such as image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with steady-state procession, and so on), a flip angle value, acquisition time (TA), echo time (TE), repetition time (TR), inversion time (TI), saturation time (TS), echo train length (ETL), the number of phases, the number of excitations (NEX), bandwidth (e.g., RF receiver bandwidth, RF transmitter bandwidth, etc.), a scan type, a type of sampling, time points when the MR data is acquired (e.g., cardiac phases, respiratory phases, etc.), or the like, or any combination thereof. The I/O may also display MR images generated based on the sampled data.

In some embodiments, the I/O 450 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
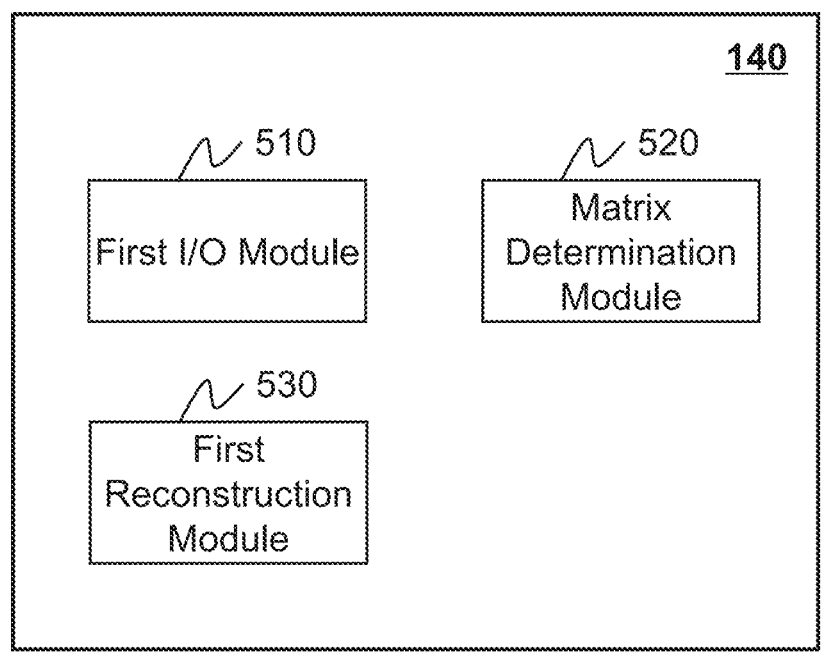
FIG. 5 is a schematic block diagram illustrating an exemplary processing device according to some embodiments of the present disclosure.

FIG. 5 is a schematic block diagram illustrating an exemplary processing device according to some embodiments of the present disclosure. The processing device 140 may include a first input/output (I/O) module 510, a matrix determination module 520, and a first reconstruction module 530.

The first I/O module 510 may obtain magnetic resonance (MR) data associated with a region of interest (ROI) of an object. The MR data may be acquired by scanning the ROI using an MRI scanner (e.g., the scanner 110 of the medical system 100 in FIG. 1) based on a plurality of parameters. The MR data may correspond to a plurality of time-series images of the ROI. In some embodiments, the ROI may be one or more regions or volumes of the object. In some embodiments, the plurality of time-series images may represent one or more dynamics of the ROI, such as T1 recovery, T2 decay, cardiac motion, respiratory motion, contrast agent dynamics, or the like, or any combination thereof.

In some embodiments, different values of the plurality of parameters may be set through the user device 130. In some embodiments, the user device 130 may transmit an instruction including the different values of the plurality of parameters to the processing device 140 to direct the processing device 140 to control the scanner 110 to scan the ROI based on the different values of the plurality of parameters. In some embodiments, the user device 130 may transmit an instruction regarding one or more relevant imaging protocols (e.g., a protocol for brain imaging, a protocol for cardiac imaging, a protocol for lung imaging, etc.). The processing device 140 may set or retrieve from a storage device (e.g., the storage device 150 and/or the storage 320 of the processing device 140) the plurality of parameters and/or different values of the plurality of parameters according to the instruction. In some embodiments, the processing device 140 may obtain an imaging plan (e.g., a prescription provided by a user or retrieved from a storage device) on the basis of which the processing device 140 may obtain (e.g., from a storage device) the plurality of parameters and/or different values of the plurality of parameters corresponding to the imaging plan. The different values of the plurality of parameters may enable the one or more dynamics of the ROI to be imaged.

In some embodiments, the plurality of parameters may include a cardiac phase, a respiratory phase, an imaging sequence parameter (e.g., an inversion time (TI), a saturation time (TS), etc.), or the like, or any combination thereof. In some embodiments, the cardiac phase may indicate a state of the heart of the object at a time point in a cardiac cycle (e.g., a heartbeat). For example, the cardiac phase may include an end-diastole phase, an end-systole phase, or the like. If the ROI includes at least a portion of the heart, different cardiac phases (e.g., different time points corresponding to the different cardiac phases) may be set to enable the dynamics of cardiac motion of the ROI to be imaged.

In some embodiments, the respiratory phase may indicate a state of the lung of the object at a time point in a respiratory cycle (e.g., a breath). For example, the respiratory phase may include an end-expiration phase, an end-inspiration phase, or the like. If the ROI includes at least a portion of the lung, different respiratory phases (e.g., different time points corresponding to the different respiratory phases) may be set to enable the dynamic of respiratory motion of the ROI to be imaged.

In an inversion recovery sequence, before the excitation RF pulse, a 180° RF pulse may be applied to rotate the magnetization into the negative plane. The interval between the 180° RF pulse and the excitation RF pulse may be referred to as the inversion time. In a saturation recovery sequence, before the excitation RF pulse, a 90° RF pulse may be applied to rotate the magnetization into the transverse plane. The interval between the 90° RF pulse and the excitation RF pulse may be referred to as the saturation time.

In some embodiments, different inversion times or saturation times may be set to enable the dynamic of T1 recovery of the ROI.

In some embodiments, the first I/O module 510 may obtain the MR data from the scanner 110 or the storage device 150.

The matrix determination module 520 may determine, based on the MR data, a data set including a spatial basis and one or more temporal bases. The spatial basis may include spatial information of the MR data. The one or more temporal bases may include temporal information of the MR data. In some embodiments, the spatial basis or the temporal basis may include a function, a model, a vector, a matrix, a tensor, or the like, or any combination thereof. In some embodiments, the matrix determination module 520 may determine the spatial basis and the one or more temporal bases based on the MR data and the low-rank model. In some embodiments, the low-rank model may represent the plurality of time-series images. In some embodiments, the low-rank model may indicate that the correlation between the plurality of time-series images is of a low rank. As used herein, low rank indicates that the rank of a model (e.g., a two-dimensional (2D) matrix or a multidimensional tensor) is smaller than the number (or count) of elements of any one dimension of the model (e.g., the column number and the row number of a matrix). Further, low rank indicates that the rank of a model is much smaller than the number (or count) of elements of any one dimension of the model. For example, the rank of the model is smaller than 50%, 40%, 30%, 20%, 10%, etc. of the minimum of the number (or count) of elements of each dimension of the model. In some embodiments, the low-rank model may take the form of the spatial basis and the one or more temporal bases that correspond to acquired MR data. Due to the low rank feature, the spatial basis and the one or more temporal bases may have a smaller file size or data volume than the plurality of time-series images. In the present disclosure, the spatial basis and the one or more temporal bases, instead of all of the plurality of time-series images, may be stored, which may reduce the storage space to be occupied.

In some embodiments, the low-rank model may include a low-rank matrix. The spatial basis may include a spatial basis matrix. The one or more temporal bases may include a temporal basis matrix.

In some embodiments, the low-rank model may include a low-rank tensor. The data set may further include a core tensor. The spatial basis may include a spatial basis matrix. The one or more temporal basis may include two or more temporal basis matrices. The low-rank tensor may be a multidimensional tensor of one spatial dimension including pixel (or voxel) locations in the plurality of time-series images and two or more time dimensions each of which corresponds to a the ROI imaged according to a set of values of one parameter of the plurality of parameters).

The first reconstruction module 530 may reconstruct at least a portion of the plurality of time-series images based on the data set. In some embodiments, the first reconstruction module 530 may reconstruct at least a portion of the plurality of time-series images based on the spatial basis and the one or more temporal bases. In some embodiments, the first reconstruction module 530 may reconstruct at least a portion of the plurality of time-series images based on the spatial basis matrix and the one or more temporal basis matrices. In some embodiments, the reconstructed images may include at least one set of images of the plurality of time-series images that indicate a variation of values of one of the plurality of parameters over time (e.g., a dynamic of the ROI). For example, as shown in column A1 in FIG. 7B, the reconstructed images may include a first set of images 702 that indicate the respiratory motion of the ROI, a second set of images 703 that indicate the cardiac motion of the ROI, and a third set of images 704 that indicate T1 recovery of the ROI. As another example, the first reconstruction module 530 may generate a fourth set of images indicate T1 recovery of the ROI and a fifth set of images indicating cardiac motion of the ROI. The first reconstruction module 530 may determine a T1 value corresponding to each pixel or voxel of the ROI based on the fourth set of images. The first reconstruction module 530 may transform the fifth set of images into false-color images (e.g., images 705 shown in column A2 in FIG. 7B) based on the T1 value corresponding to each pixel or voxel of the ROI. In some embodiments, the first reconstruction module 530 may designate a color value for each T1 value. Merely by way of example, the T1 values of the pixels or voxels of the fifth set of images may be within a range of 0-3 seconds. The first reconstruction module 530 may determine a color bar 701 (e.g., as shown in column A2 in FIG. 7B) including color values for the T1 values. The first reconstruction module 530 may generate the false-color images by transforming the gray value of each pixel or voxel in the fifth set of images into the corresponding color value. The false-color images may represent T1 values and the cardiac motion of the ROI. As a further example, the reconstructed images may include one or more other images of the plurality of time-series images which are of the user's interest (e.g., the one or more other images may be displayed in column A3 in FIG. 7B), such as one or more images of end-diastole or end-systole.

In some embodiments, a reconstruction instruction indicating which of the plurality of time-series images are needed to be reconstructed may be set in the scan protocol through, e.g., the user device 130. For example, the reconstruction instruction may include a value of at least one of the plurality of parameters corresponding to each of the portion of the plurality of time-series image. For example, the ROI of the object may be scanned based on the plurality of parameters including 20 cardiac phases, 5 respiratory phases, and 344 inversion times. If a set of images of the plurality of time-series images that indicate T1 recovery of the ROI are needed to be reconstructed, the reconstruction instruction may include one of the 20 cardiac phases, one of the 5 respiratory phases, and the 344 inversion times.

In some embodiments, the reconstruction instruction may be obtained according to a default setting of the medical system 100. In some embodiments, the reconstruction instruction may be manually set by the user or automatically set by the user device 130 based on, e.g., imaging protocol or plan (e.g., prescription) of the ROI and/or the clinical need of the user and/or the object (e.g., the patient). For example, in T1 mapping, the reconstruction instruction may indicate reconstructing a set of images that indicate T1 recovery of the ROI.

In some embodiments, the first reconstruction module 530 may reconstruct the portion of the plurality of time-series images based on operations 930 and 940 of the process 900 in FIG. 9.

In some embodiments, the first I/O module 510 may transmit the reconstructed images to the user device 130 and direct the user device 130 to display the reconstructed images in an interface of the user device 130. For example, as shown in FIG. 7B, the reconstructed images may include a first set of images 702 that indicate the respiratory motion of the ROI, a second set of images 703 that indicate the cardiac motion of the ROI, a third set of images 704 that indicate T1 recovery of the ROI, a set of false-color images 705 representing T1 values and the cardiac motion of the ROI, and one or more other images of the plurality of time-series images which are of the user's interest. The user device 130 may display the first set of images 702, the second set of images 703, and the third set of images 704 in column A1. The user device 130 may display the set of false-color images 705 in column A2. The user device 130 may display the one or more other images of the user's interest in column A3. In some embodiments, the user device 130 may simultaneously display at least one of column A1, column A2, and column A3 in the interface of the user device 130.

The first I/O module 510 may store, in a storage device, the reconstructed images and at least a portion of the data set. In some embodiments, the first I/O module 510 may store, in the storage device, the spatial basis and the one or more temporal bases. In some embodiments, the first I/O module 510 may store, in the storage device, the spatial basis matrix and the temporal basis matrix. In some embodiments, the first I/O module 510 may store, in the storage device, the spatial basis matrix, the two or more temporal basis matrices, and the core tensor. In some embodiments, the first I/O module 510 may store, in the storage device, a combination (e.g., a product) of the core tensor and at least one of the spatial basis matrix and the two or more temporal basis matrices. Further, the first I/O module 510 may store, in the storage device, a combination (e.g., a product) of the core tensor and the spatial basis matrix. In some embodiments, the storage device may include the storage device 150 and/or the storage 320 of the processing device 140. In some embodiments, the user may use the user device 130 to access the storage device to obtain the reconstructed images and the stored data set.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the first I/O module 510 may be divided into two units. One of the two unit may be configured to obtain MR data from the scanner 110, and the other one of the two unit may be configured to transmit a spatial basis matrix and one or more temporal basis matrices to the storage device 150, and/or transmit the reconstructed images to the user device 130 to be displayed.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of the processing device 140. As another example, each of the components of the processing device 140 may include a storage device. Additionally or alternatively, the components of the processing device 140 may share a common storage device. As a further example, the first reconstruction module 530 may be omitted.

FIG. 6 is a flowchart illustrating an exemplary process for MRI reconstruction according to some embodiments of the present disclosure. In some embodiments, the process 600 may be implemented in the medical system 100 illustrated in FIG. 1. For example, the process 600 may be stored in a storage medium (e.g., the storage device 150, or the storage 320 of the processing device 140) as a form of instructions, and can be invoked and/or executed by the processing device 140 (e.g., the processor 310 of the processing device 140, or one or more modules in the processing device 140 illustrated in FIG. 5). The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 140 (e.g., the first I/O module 510) may obtain magnetic resonance (MR) data associated with a region of interest (ROI) of an object. The MR data may be acquired by scanning the ROI using an MRI scanner (e.g., the scanner 110 of the medical system 100 in FIG. 1) based on a plurality of parameters. The MR data may correspond to a plurality of time-series images of the ROI. In some embodiments, the ROI may be one or more regions or volumes of the object. In some embodiments, the plurality of time-series images may represent one or more dynamics of the ROI, such as T1 recovery, T2 decay, cardiac motion, respiratory motion, contrast agent dynamics, or the like, or any combination thereof.

In some embodiments, different values of the plurality of parameters may be set through the user device 130. In some embodiments, the user device 130 may transmit an instruction including the different values of the plurality of parameters to the processing device 140 to direct the processing device 140 to control the scanner 110 to scan the ROI based on the different values of the plurality of parameters. In some embodiments, the user device 130 may transmit an instruction regarding one or more relevant imaging protocols (e.g., a protocol for brain imaging, a protocol for cardiac imaging, a protocol for lung imaging, etc.). The processing device 140 may set or retrieve from a storage device (e.g., the storage device 150 and/or the storage 320 of the processing device 140) the plurality of parameters and/or different values of the plurality of parameters according to the instruction. In some embodiments, the processing device 140 may obtain an imaging plan (e.g., a prescription provided by a user or retrieved from a storage device) on the basis of which the processing device 140 may obtain (e.g., from a storage device) the plurality of parameters and/or different values of the plurality of parameters corresponding to the imaging plan. The different values of the plurality of parameters may enable the one or more dynamics of the ROI to be imaged.

In some embodiments, the plurality of parameters may include a cardiac phase, a respiratory phase, an imaging sequence parameter (e.g., an inversion time (TI), a saturation time (TS), etc.), or the like, or any combination thereof. In some embodiments, the cardiac phase may indicate a state of the heart of the object at a time point in a cardiac cycle (e.g., a heartbeat). For example, the cardiac phase may include an end-diastole phase, an end-systole phase, or the like. If the ROI includes at least a portion of the heart, different cardiac phases (e.g., different time points corresponding to the different cardiac phases) may be set to enable the dynamics of cardiac motion of the ROI to be imaged.

In some embodiments, the respiratory phase may indicate a state of the lung of the object at a time point in a respiratory cycle (e.g., a breath). For example, the respiratory phase may include an end-expiration phase, an end-inspiration phase, or the like. If the ROI includes at least a portion of the lung, different respiratory phases (e.g., different time points corresponding to the different respiratory phases) may be set to enable the dynamic of respiratory motion of the ROI to be imaged.

In an inversion recovery sequence, before the excitation RF pulse, a 180° RF pulse may be applied to rotate the magnetization into the negative plane. The interval between the 180° RF pulse and the excitation RF pulse may be referred to as the inversion time. In a saturation recovery sequence, before the excitation RF pulse, a 90° RF pulse may be applied to rotate the magnetization into the transverse plane. The interval between the 90° RF pulse and the excitation RF pulse may be referred to as the saturation time. In some embodiments, different inversion times or saturation times may be set to enable the dynamic of T1 recovery of the ROI.

In some embodiments, the processing device 140 may obtain the MR data from the scanner 110 or the storage device 150.

In 620, the processing device 140 (e.g., the matrix determination module 520) may determine, based on the MR data, a data set including a spatial basis and one or more temporal bases. The spatial basis may include spatial information of the MR data. The one or more temporal bases may include temporal information of the MR data. In some embodiments, the spatial basis or the temporal basis may include a function, a model, a vector, a matrix, a tensor, or the like, or any combination thereof.

In some embodiments, in addition to the spatial correlation of information represented in the plurality of time-series images, temporal correlation may also exist in the information represented in the plurality of time-series images. Taking the cardiac dynamic magnetic resonance images as an example, due to the approximately periodic motion of the heart, variations of values of neighboring pixels (or voxels) over time may be similar. This similarity may be converted to the low-rank feature of a model representing the plurality of time-series images for image reconstruction.

In some embodiments, the processing device 140 may determine the spatial basis and the one or more temporal bases based on the MR data and the low-rank model. In some embodiments, the low-rank model may represent the plurality of time-series images. In some embodiments, the low-rank model may indicate that the correlation between the plurality of time-series images is of a low rank. As used herein, low rank indicates that the rank of a model (e.g., a two-dimensional (2D) matrix or a multidimensional tensor) is smaller than the number (or count) of elements of any one dimension of the model (e.g., the column number and the row number of a matrix). Further, low rank indicates that the rank of a model is much smaller than the number (or count) of elements of any one dimension of the model. For example, the rank of the model is smaller than 50%, 40%, 30%, 20%, 10%, etc. of the minimum of the number (or count) of elements of each dimension of the model. In some embodiments, the low-rank model may take the form of the spatial basis and the one or more temporal bases that correspond to acquired MR data. Due to the low rank feature, the spatial basis and the one or more temporal bases may have a smaller file size or data volume than the plurality of time-series images. In the present disclosure, the spatial basis and the one or more temporal bases, instead of all of the plurality of time-series images, may be stored, which may reduce the storage space to be occupied.

In some embodiments, the low-rank model may include a low-rank matrix. The spatial basis may include a spatial basis matrix. The one or more temporal bases may include a temporal basis matrix. For example, f(y, t) may refer to a space-time signal of the MR data, γ may refer to a location (e.g., two-dimensional (2D) coordinates (x, y) or three-dimensional (3D) coordinates (x, y, z)) in the ROI (a location of a pixel or voxel in the plurality of time-series images), and t may refer to a time point. The low-rank matrix F may be represented as Equation (1) below:

$$F = \begin{bmatrix} f(\gamma_1, t_1) & \cdots & f(\gamma_1, t_n) \\ f(\gamma_2, t_1) & \cdots & f(\gamma_2, t_n) \\ \vdots & \ddots & \vdots \\ f(\gamma_m, t_1) & \cdots & f(\gamma_m, t_n) \end{bmatrix}, \quad (1)$$

wherein m refers to the number (or count) of pixels (or voxels) in each of the plurality of time-series images; n refers to the number (or count) of the plurality of time-series images; each column in the low-rank matrix F represents one of the plurality of time-series images; and each row in the low-rank matrix F indicates the variation, over time, of the signal intensity (or the gray value) of the pixels (or voxels) in the plurality of time-series images that correspond to the same location in the ROI.

In each of the plurality of time-series images, differences between the values of the pixels (or voxels) may be relatively small. Variations, over time, of values of neighboring pixels (or voxels) in the plurality of time-series images may be similar. Therefore, there may be a relatively strong correlation among the row vectors of the matrix F and also a relatively strong correlation among the column vectors of the matrix F, which makes the matrix F have the low rank feature, e.g., the rank of Fr<min(m, n).

In some embodiments, f(γ, t) may refer to MR images with different contrast. Such as images acquired at different TE, different TR, and different flip angles. There may be a relatively strong correlation among the row vectors of the matrix F and also a relatively strong correlation among the column vectors of the matrix F, which makes the matrix F have the low rank feature, e.g., the rank of Fr<min(m, n).

In some embodiments, the low-rank model F may be decomposed into a spatial basis matrix Us and a temporal basis matrix Vt based on singular value decomposition (SVD):

$$F = UsVt^T. \quad (2)$$

In some embodiments, the spatial basis matrix Us may include signals of the MR data corresponding to pixels (or voxels) in the plurality of time-series images and index locations of the pixels (or voxels) in the plurality of time-series images. The temporal basis matrix Vt may include a plurality of time points each of which represents an imaging time of one of the plurality of time-series images, and the plurality of time points may correspond to the elapsed time of the whole scan process of the ROI.

In some embodiments, the low-rank matrix F may include m×n elements, the spatial basis matrix Us may include m×r elements, and the temporal basis matrix Vt may include r×n elements, wherein r refers to the rank of the low-rank matrix F. In the present disclosure, the spatial basis matrix Us and the temporal basis matrix Vt (e.g., r(m+n) elements), instead of all of the plurality of time-series images (e.g., m×n elements), may be stored. Because of the low rank feature of the matrix F, r may be less than, even far less than, m and n, which may reduce the data volume and/or file size for storage and/or transmission.

In some embodiments, the processing device 140 may determine the spatial basis matrix U's including m×r' elements and the temporal basis matrix VT including r'×n elements, wherein r' is less than the rank of the low-rank matrix F. The combination of the spatial basis matrix U's and the temporal basis matrix V't may approximate the low-rank matrix F. Presentation of the acquired MR data in the form of the spatial basis matrix U's and the temporal basis matrix V't (e.g., storing r'(m+n) elements) may further reduce the data volume and/or file size for storage and/or transmission, and reduce noise of the plurality of time-series images.

In some embodiments, the processing device 140 may determine the spatial basis matrix and the temporal basis matrix based on singular value decomposition (SVD) of already acquired or reconstructed image series.

In some embodiments, the low-rank model may include a low-rank tensor. The data set may further include a core tensor. The spatial basis may include a spatial basis matrix. The one or more temporal basis may include two or more temporal basis matrices. The low-rank tensor may be a multidimensional tensor of one spatial dimension including pixel (or voxel) locations in the plurality of time-series images and two or more time dimensions each of which corresponds to a the ROI imaged according to a set of values of one parameter of the plurality of parameters).

In each of the plurality of time-series images, differences between the values of the pixels (or voxels) may be relatively small. Variations, over time, of values of neighboring pixels (or voxels) in the plurality of time-series images may be similar. Therefore, the tensor may have the low rank feature.

In some embodiments, the low-rank tensor may be decomposed into a core tensor, a spatial basis matrix, and two or more temporal basis matrices based on Tucker decomposition.

In some embodiments, the spatial basis matrix may correspond to the spatial dimension of the low-rank tensor. The spatial basis matrix may include signals of the MR data corresponding to pixels (or voxels) in the plurality of time-series images and index locations of the pixels (or voxels) in the plurality of time-series images. Each of the two or more temporal basis matrices may correspond to one of the two or more time dimensions of the low-rank tensor.

For example, the ROI of the object may be scanned based on the plurality of parameters including 20 cardiac phases, 5 respiratory phases, and 344 inversion times. The low-rank tensor may be a 4-way tensor including a spatial dimension and 3 time dimensions that correspond to the cardiac motion, the respiratory motion, and the T1 recovery, respectively. A core tensor, a spatial basis matrix corresponding to the spatial dimension, and 3 temporal basis matrices corresponding to the 3 time dimensions may be determined. A first temporal basis matrix of the 3 temporal basis matrices may correspond to the time dimension of cardiac motion of the low-rank tensor and index the 20 cardiac phases (e.g., 20 time points corresponding to the 20 cardiac phases). A second temporal basis matrix of the 3 temporal basis matrices may correspond to the time dimension of respiratory motion of the low-rank tensor and index the 5 respiratory phases (e.g., 5 time points corresponding to the 5 respiratory phases). A third temporal basis matrix of the 3 temporal basis matrices may correspond to the time dimension of T1 recovery of the low-rank tensor and index the 344 inversion times.

Figure 7A:
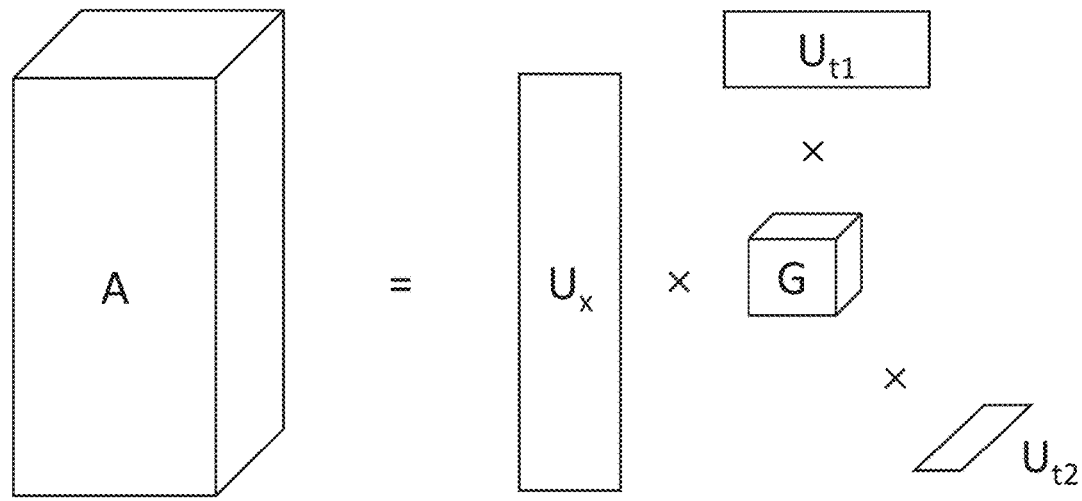
FIG. 7A shows an exemplary illustration of Tucker factorization of a low-rank 3-way tensor according to some embodiments of the present disclosure.
Figure 7B:
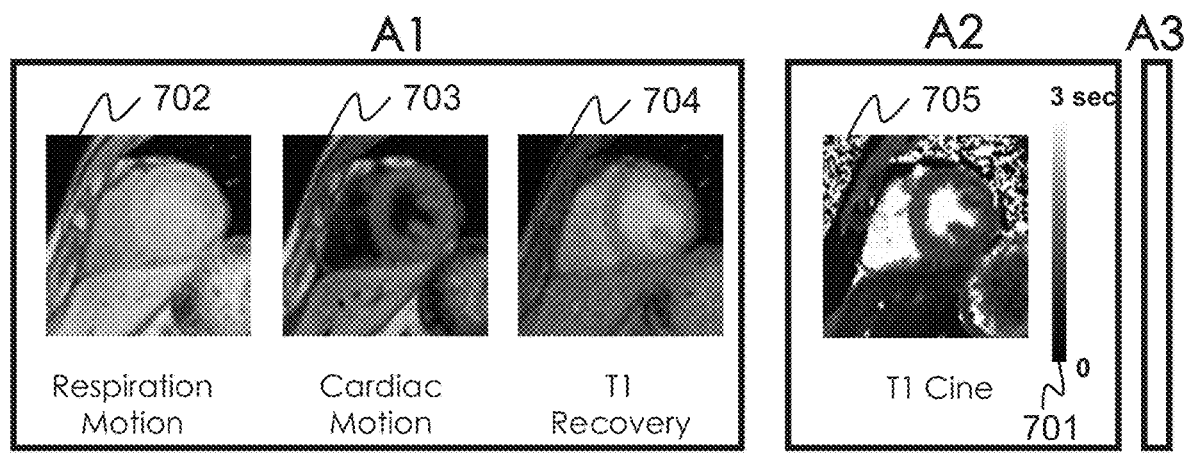
FIG. 7B shows an exemplary illustration of a portion of a plurality of time-series images according to some embodiments of the present disclosure.

Merely by way of example, FIG. 7A shows an exemplary illustration of Tucker factorization of a low-rank 3-way tensor according to some embodiments of the present disclosure. The low-rank tensor A may include a spatial dimension and two time dimensions. As shown in FIG. 7A, according to Tucker decomposition, the low-rank tensor A may be decomposed into a core tensor G, a spatial basis matrix Ux corresponding to the spatial dimension, and two temporal basis matrices $Ut_1$ and $Ut_2$ corresponding to the two time dimensions, respectively.

The low-rank tensor A may include J×K×L elements, the spatial basis matrix Ux may include J×$r_1$ elements, the temporal basis matrix $Ut_1$ may include K×$r_2$ elements, the temporal basis matrix $Ut_2$ may include L×$r_3$ elements, and the core tensor G may include $r_1 \times r_2 \times r_3$ elements, wherein $r_1$ refers to the rank of the spatial basis matrix Ux, $r_2$ refers to the rank of the temporal basis matrix $Ut_1$, and $r_3$ refers to the rank of the temporal basis matrix $Ut_2$. In the present disclosure, the core tensor G, the spatial basis matrix Ux, and the two temporal basis matrices $Ut_1$ and $Ut_2$ (e.g., $r_1 r_2 r_3 + Jr_1 + Kr_2 + Lr_3$ elements), instead of all of the plurality of time-series images (e.g., J×K×L elements), may be stored. Because of the low rank feature of the tensor A, $r_1$, $r_2$, and $r_3$ may be less than, even far less than, J, K, and L, which may reduce the data volume and/or file size for storage and/or transmission.

In some embodiments, the processing device 140 may determine the spatial basis matrix U'x including J×$r'_1$ elements, the temporal basis matrix $U't_1$ including K×$r'_2$ elements, the temporal basis matrix $U't_2$ including L×$r'_3$ elements, and the core tensor G' including $r'_1 \times r'_2 \times r'_3$ elements, wherein $r'_1$ is less than the rank of the spatial basis matrix U'x, $r'_2$ is less than the rank of the temporal basis matrix $U't_1$, and $r_3$ is less than the rank of the temporal basis matrix $U't_2$. The combination of the spatial basis matrix U'x, the temporal basis matrix $U't_1$, the temporal basis matrix $U't_2$, and the core tensor G' may approximate the low-rank tensor A. Presentation of the acquired MR data in the form of the spatial basis matrix U'x, the temporal basis matrix $U't_1$, the temporal basis matrix $U't_2$, and the core tensor G' (e.g., $r'_1 r'_2 r'_3 + Jr'_1 + Kr'_2 + Lr'_3$ elements) may further reduce the data volume and/or file size for storage and/or transmission, and reduce noise of the plurality of time-series images.

In some embodiments, the processing device 140 may determine the core tensor, the spatial basis matrix, and the two or more temporal basis matrices based on Tucker decomposition of already acquired or reconstructed image series. In 630, the processing device 140 (e.g., the first reconstruction module 530) may reconstruct at least a portion of the plurality of time-series images based on the data set. In some embodiments, the processing device 140 may reconstruct at least a portion of the plurality of time-series images based on the spatial basis and the one or more temporal bases. In some embodiments, the processing device 140 may reconstruct at least a portion of the plurality of time-series images based on the spatial basis matrix and the one or more temporal basis matrices. In some embodiments, the reconstructed images may include at least one set of images of the plurality of time-series images that indicate a variation of values of one of the plurality of parameters over time (e.g., a dynamic of the ROI). For example, as shown in column A1 in FIG. 7B, the reconstructed images may include a first set of images 702 that indicate the respiratory motion of the ROI, a second set of images 703 that indicate the cardiac motion of the ROI, and a third set of images 704 that indicate T1 recovery of the ROI. As another example, the processing device 140 may generate a fourth set of images indicate T1 recovery of the ROI and a fifth set of images indicating cardiac motion of the ROI. The processing device 140 may determine a T1 value corresponding to each pixel or voxel of the ROI based on the fourth set of images. The processing device 140 may transform the fifth set of images into false-color images (e.g., images 705 shown in column A2 in FIG. 7B) based on the T1 value corresponding to each pixel or voxel of the ROI. In some embodiments, the processing device 140 may designate a color value for each T1 value. Merely by way of example, the T1 values of the pixels or voxels of the fifth set of images may be within the range of 0-3 seconds. The processing device 140 may determine a color bar 701 (e.g., as shown in column A2 in FIG. 7B) including color values for the T1 values. The processing device 140 may generate the false-color images by transforming the gray value of each pixel or voxel in the fifth set of images into the corresponding color value. The false-color images may represent T1 values and the cardiac motion of the ROI. As a further example, the reconstructed images may include one or more other images of the plurality of time-series images which are of the user's interest (e.g., as shown in column A3 in FIG. 7B), such as one or more images of end-diastole or end-systole.

In some embodiments, a reconstruction instruction indicating which of the plurality of time-series images are needed to be reconstructed may be set in the scan protocol through, e.g., the user device 130. For example, the reconstruction instruction may include a value of at least one of the plurality of parameters corresponding to each of the portion of the plurality of time-series image. For example, the ROI of the object may be scanned based on the plurality of parameters including 20 cardiac phases, 5 respiratory phases, and 344 inversion times. If a set of images of the plurality of time-series images that indicate T1 recovery of the ROI are needed to be reconstructed, the reconstruction instruction may include one of the 20 cardiac phases, one of the 5 respiratory phases, and the 344 inversion times.

In some embodiments, the reconstruction instruction may be obtained according to a default setting of the medical system 100. In some embodiments, the reconstruction instruction may be manually set by the user or automatically set by the user device 130 based on, e.g., imaging protocol or plan (e.g., prescription) of the ROI and/or the clinical need of the user and/or the object (e.g., the patient). For example, in T1 mapping, the reconstruction instruction may indicate reconstructing a set of images that indicate T1 recovery of the ROI.

In some embodiments, the processing device 140 may reconstruct the portion of the plurality of time-series images based on operations 930 and 940 of the process 900 in FIG. 9.

In some embodiments, the processing device 140 may transmit the reconstructed images to the user device 130 and direct the user device 130 to display the reconstructed images in an interface of the user device 130. For example, as shown in FIG. 7B, the reconstructed images may include a first set of images 702 that indicate the respiratory motion of the ROI, a second set of images 703 that indicate the cardiac motion of the ROI, a third set of images 704 that indicate T1 recovery of the ROI, a set of false-color images 705 representing T1 values and the cardiac motion of the ROI, and one or more other images of the plurality of time-series images which are of the user's interest. The user device 130 may display the first set of images 702, the second set of images 703, and the third set of images 704 in column A1. The user device 130 may display the set of false-color images 705 in column A2. The user device 130 may display the one or more other images of the user's interest in column A3. In some embodiments, the user device 130 may simultaneously display at least one of column A1, column A2, and column A3 in the interface of the user device 130.

In 640, the processing device 140 (e.g., the first I/O module 510) may store, in a storage device, the reconstructed images and at least a portion of the data set. In some embodiments, the processing device 140 may store, in the storage device, the spatial basis and the one or more temporal bases. In some embodiments, the processing device 140 may store, in the storage device, the spatial basis matrix and the temporal basis matrix. In some embodiments, the processing device 140 may store, in the storage device, the spatial basis matrix, the two or more temporal basis matrices, and the core tensor. In some embodiments, the processing device 140 may store, in the storage device, a combination (e.g., a product) of the core tensor and at least one of the spatial basis matrix and the two or more temporal basis matrices. Further, the processing device 140 may store, in the storage device, a combination (e.g., a product) of the core tensor and the spatial basis matrix. In some embodiments, the storage device may include the storage device 150 and/or the storage 320 of the processing device 140. In some embodiments, the user may use the user device 130 to access the storage device to obtain the reconstructed images and the stored data set.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 630 may be performed before, after, or simultaneously with the operation of storing, in the storage device, the spatial basis matrix and the one or more temporal basis matrices. As another example, operation 630 may be omitted.

Figure 8:
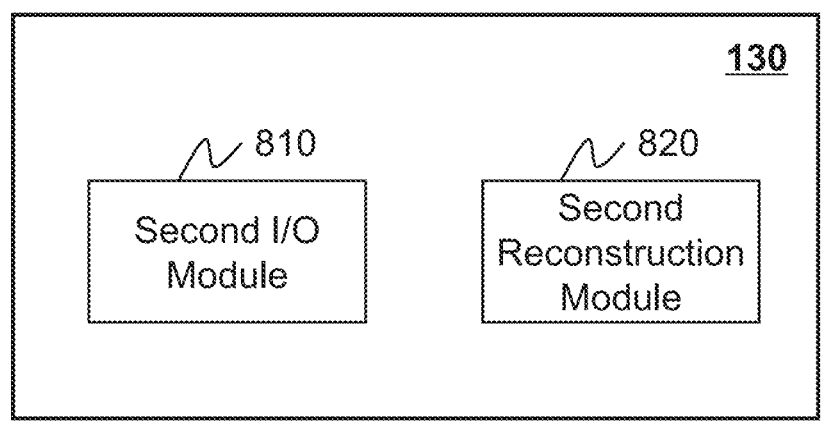
FIG. 8 is a schematic block diagram illustrating an exemplary user device according to some embodiments of the present disclosure.

FIG. 8 is a schematic block diagram illustrating an exemplary user device according to some embodiments of the present disclosure. The processing device 140 may include a second input/output (I/O) module 810 and a second reconstruction module 820.

The second I/O module 810 may obtain, from a storage device, a data set including a spatial basis and one or more temporal bases. The spatial basis and the one or more temporal bases may correspond to a plurality of time-series images of a region of interest (ROI) of an object. The spatial basis may include spatial information of the plurality of time-series images. The one or more temporal bases may include temporal information of the plurality of time-series images. In some embodiments, the spatial basis or the temporal basis may include a function, a model, a vector, a matrix, a tensor, or the like, or any combination thereof.

In some embodiments, the second I/O module 810 may obtain a spatial basis matrix and a temporal basis matrix, the combination of which represents a low-rank matrix corresponding to the plurality of time-series images. In some embodiments, the data set may further include a core tensor. The second I/O module 810 may obtain a core tensor, a spatial basis matrix, and two or more temporal basis matrices, the combination of which represents a low-rank tensor corresponding to the plurality of time-series images. In some embodiments, the second I/O module 810 may obtain a combination (e.g., a product) of the core tensor and at least one of the spatial basis matrix and the two or more temporal basis matrices. In some embodiments, the second I/O module 810 may obtain the two or more temporal basis matrices and a combination (e.g., a product) of the core tensor and the spatial basis matrix.

The second I/O module 810 may receive an instruction for reconstructing one or more target images of the plurality of time-series images.

In some embodiments, the instruction may include a value of at least one of the plurality of parameters corresponding to each of the one or more target images. For example, the ROI of the object may be scanned based on the plurality of parameters including 20 cardiac phases, 5 respiratory phases, and 344 inversion times. The user may select one of the 20 cardiac phases, one of the 5 respiratory phases, and one of the 344 inversion times in an interface of the user device 130 to generate an instruction of reconstructing a target image of the plurality of time-series images.

The second reconstruction module 820 may reconstruct the one or more target images based on the data set and the instruction. In some embodiments, the second reconstruction module 820 may determine, for each of the one or more target images, a temporal basis sub-set of each of the one or more temporal bases based on the instruction. The second reconstruction module 820 may reconstruct the target image based on the data set and the one or more temporal basis sub-sets.

In some embodiments, the second reconstruction module 820 may determine time information corresponding to the target image of the one or more temporal basis matrices based on the value of the at least one of the plurality of parameters in the instruction. The second reconstruction module 820 may determine, based on the time information, a temporal basis sub-matrix of each of the one or more temporal basis matrices.

In some embodiments, the second reconstruction module 820 may determine a spatial basis matrix Us and a temporal basis matrix Vt based on the MR data and a low-rank matrix corresponding to the plurality of time-series image. The temporal basis matrix Vt may include a plurality of time points each of which represents an imaging time of one of the plurality of time-series images. The plurality of time points may represent the elapsed time of the whole scan process of the ROI. The second reconstruction module 820 may determine a time point n corresponding to the target image based on the instruction. For example, the ROI of the object may be scanned based on the plurality of parameters including 20 cardiac phases, 5 respiratory phases, and 344 inversion times. The user may generate an instruction for reconstructing the target image by specifying which of the 20 cardiac phases, which of the 5 respiratory phases, and/or which of the 344 inversion times for the image reconstruction. The second reconstruction module 820 may determine the time point n corresponding to the target image based on the selected cardiac phase, respiratory phase, and inversion time in the instruction. In some embodiments, the second reconstruction module 820 may determine the temporal basis sub-matrix Vt(n) of the temporal basis matrix Vt based on the time point n.

In some embodiments, the processing device 140 may determine a core tensor G, a spatial basis matrix Ux, and N temporal basis matrices $Ut_1, Ut_2, \ldots, Ut_N$ based on the MR data and a low-rank N+1-way tensor corresponding to the plurality of time-series image. Each of the N temporal basis matrices may correspond to one of the N time dimensions of the low-rank N+1-way tensor and index different values of one of the plurality of parameters. For each of the N temporal basis matrices, the second reconstruction module 820 may determine a time point, along the corresponding time dimension, based on the value of the corresponding parameter in the instruction. For example, the ROI of the object may be scanned based on the plurality of parameters including 20 cardiac phases, 5 respiratory phases, and 344 inversion times. The user may generate the instruction for reconstructing the target image by specifying which of the 20 cardiac phases, which of the 5 respiratory phases, and/or which of the 344 inversion times for the image reconstruction. The second reconstruction module 820 may determine the time point n, along the time dimension of cardiac motion based on the selected cardiac phase in the instruction. The second reconstruction module 820 may determine the time point $n_2$ along the time dimension of respiratory motion based on the selected respiratory phase in the instruction. The second reconstruction module 820 may determine the time point $n_3$ along the time dimension of T1 recovery based on the selected inversion time in the instruction. In some embodiments, the second reconstruction module 820 may determine the temporal basis sub-matrix $Ut_1(n_1)$, $Ut_2(n_2)$, ..., $Ut_N(n_N)$ of each of the two or more temporal basis matrices $Ut_1$, $Ut_2$, ..., $Ut_N$ based on the time points $n_1$, $n_2$, ..., $n_N$.

In some embodiments, the second reconstruction module 820 may reconstruct the target image based on the spatial basis matrix and the one or more temporal basis sub-matrices.

In some embodiments, the spatial basis matrix may include signals of different pixel (or voxel) locations of the plurality of time-series images at different time points. The operation of generating the target image based on the temporal basis sub-matrix of each of the one or more temporal basis matrices and the spatial basis matrix may be regarded as using the temporal basis sub-matrix of each of the one or more temporal basis matrices to extract the target image from the spatial basis matrix.

In some embodiments, the second reconstruction module 820 may generate the target image by determining a product of the spatial basis matrix Us and the temporal basis sub-matrix Vt(n) of the temporal basis matrix Vt.

In some embodiments, the second reconstruction module 820 may generate the target image by determining a product of the core tensor G, the spatial basis matrix Ux, and the temporal basis sub-matrix $Ut_1(n_1)$, $Ut_2(n_2)$, ..., $Ut_N(n_N)$ of each of the N temporal basis matrices $Ut_1$, $Ut_2$, ..., $Ut_N$.

The second I/O module 810 may display the one or more target images.

The second I/O module 810 may store at least one of the one or more target images in the storage device.

The modules in the user device 130 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the second VO module 810 may be divided into two units. One of the two units may be configured to obtain the spatial basis matrix and the one or more temporal basis matrices from the storage medium, and the other one of the two units may be configured to transmit one or more reconstructed images to the storage medium.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the user device 130 may further include a storage module (not shown in FIG. 8). The storage module may be configured to store data generated during any process performed by any component of the user device 130. As another example, each of the components of the user device 130 may include a storage device. Additionally or alternatively, the components of the user device 130 may share a common storage device.

FIG. 9 is a flowchart illustrating an exemplary process for MRI reconstruction according to some embodiments of the present disclosure. In some embodiments, the process 900 may be implemented in the medical system 100 illustrated in FIG. 1. For example, the process 900 may be stored in a storage medium (e.g., the storage device 150, the storage 490 of the user device 130, or the memory 460 of the user device 130) as a form of instructions, and can be invoked and/or executed by the user device 130 (e.g., the CPU 440 of the user device 130, the GPU 430 of the user device 130, or one or more modules in the user device 130 illustrated in FIG. 8). The operations of the illustrated process 900 presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In some embodiments, when a user desires to view one or more of the plurality of time-series image (also referred to as one or more target images) on the user device 130, the user device 130 may perform the process 900.

In 910, the user device 130 (e.g., the second I/O module 810) may obtain, from a storage device, a data set including a spatial basis and one or more temporal bases. The spatial basis and the one or more temporal bases may correspond to a plurality of time-series images of a region of interest (ROI) of an object. The spatial basis may include spatial information of the plurality of time-series images. The one or more temporal bases may include temporal information of the plurality of time-series images. In some embodiments, the spatial basis or the temporal basis may include a function, a model, a vector, a matrix, a tensor, or the like, or any combination thereof.

In some embodiments, the user device 130 may obtain a spatial basis matrix and a temporal basis matrix, the combination of which represents a low-rank matrix corresponding to the plurality of time-series images. In some embodiments, the data set may further include a core tensor. The user device 130 may obtain a core tensor, a spatial basis matrix, and two or more temporal basis matrices, the combination of which represents a low-rank tensor corresponding to the plurality of time-series images. In some embodiments, the user device 130 may obtain a combination (e.g., a product) of the core tensor and at least one of the spatial basis matrix and the two or more temporal basis matrices. In some embodiments, the user device 130 may obtain the two or more temporal basis matrices and a combination (e.g., a product) of the core tensor and the spatial basis matrix.

In 920, the user device 130 (e.g., the second I/O module 810) may receive an instruction for reconstructing one or more target images of the plurality of time-series images.

In some embodiments, the instruction may include a value of at least one of the plurality of parameters corresponding to each of the one or more target images. For example, the ROI of the object may be scanned based on the plurality of parameters including 20 cardiac phases, 5 respiratory phases, and 344 inversion times. The user may select one of the 20 cardiac phases, one of the 5 respiratory phases, and one of the 344 inversion times in an interface of the user device 130 to generate an instruction of reconstructing a target image of the plurality of time-series images.

In some embodiments, the user device 130 (e.g., the second reconstruction module 820) may reconstruct the one or more target images based on the data set and the instruction. For example, the user device 130 may reconstruct the one or more target images by performing operations 930 and 940 in the process 900.

In 930, the user device 130 (e.g., the second reconstruction module 820) may determine, for each of the one or more target images, a temporal basis sub-set of each of the one or more temporal bases based on the instruction.

In some embodiments, the user device 130 may determine time information corresponding to the target image of the one or more temporal basis matrices based on the value of the at least one of the plurality of parameters in the instruction. The user device 130 may determine, based on the time information, a temporal basis sub-matrix of each of the one or more temporal basis matrices.

In some embodiments, the processing device 140 may determine a spatial basis matrix Us and a temporal basis matrix Vt based on the MR data and a low-rank matrix corresponding to the plurality of time-series image. The temporal basis matrix Vt may include a plurality of time points each of which represents an imaging time of one of the plurality of time-series images. The plurality of time points may represent the elapsed time of the whole scan process of the ROI. The user device 130 may determine a time point n corresponding to the target image based on the instruction. For example, the ROI of the object may be scanned based on the plurality of parameters including 20 cardiac phases, 5 respiratory phases, and 344 inversion times. The user may generate an instruction for reconstructing the target image by specifying which of the 20 cardiac phases, which of the 5 respiratory phases, and/or which of the 344 inversion times for the image reconstruction. The user device 130 may determine the time point n corresponding to the target image based on the selected cardiac phase, respiratory phase, and inversion time in the instruction. In some embodiments, the user device 130 may determine the temporal basis sub-matrix Vt(n) of the temporal basis matrix Vt based on the time point n.

In some embodiments, the processing device 140 may determine a core tensor G, a spatial basis matrix Ux, and N temporal basis matrices $Ut_1, Ut_2, \ldots, Ut_N$ based on the MR data and a low-rank N+1-way tensor corresponding to the plurality of time-series image. Each of the N temporal basis matrices may correspond to one of the N time dimensions of the low-rank N+1-way tensor and index different values of one of the plurality of parameters. For each of the N temporal basis matrices, the user device 130 may determine a time point, along the corresponding time dimension, based on the value of the corresponding parameter in the instruction. For example, the ROI of the object may be scanned based on the plurality of parameters including 20 cardiac phases, 5 respiratory phases, and 344 inversion times. The user may generate the instruction for reconstructing the target image by specifying which of the 20 cardiac phases, which of the 5 respiratory phases, and/or which of the 344 inversion times for the image reconstruction. The user device 130 may determine the time point $n_1$ along the time dimension of cardiac motion based on the selected cardiac phase in the instruction. The user device 130 may determine the time point $n_2$ along the time dimension of respiratory motion based on the selected respiratory phase in the instruction. The user device 130 may determine the time point $n_3$ along the time dimension of T1 recovery based on the selected inversion time in the instruction. In some embodiments, the user device 130 may determine the temporal basis sub-matrix $Ut_1(n_1), Ut_2(n_2), \ldots, Ut_N(n_N)$ of each of the two or more temporal basis matrices $Ut_1, Ut_2, \ldots, Ut_N$ based on the time points $n_1, n_2, \ldots, n_N$.

In 940, the user device 130 (e.g., the second reconstruction module 820) may reconstruct the target image based on the data set and the one or more temporal basis sub-sets. In some embodiments, the user device 130 may reconstruct the target image based on the spatial basis and the one or more temporal basis sub-sets.

In some embodiments, the spatial basis matrix may include signals of different pixel (or voxel) locations of the plurality of time-series images at different time points. The operation of generating the target image based on the temporal basis sub-matrix of each of the one or more temporal basis matrices and the spatial basis matrix may be regarded as using the temporal basis sub-matrix of each of the one or more temporal basis matrices to extract the target image from the spatial basis matrix.

In some embodiments, the user device 130 may generate the target image by determining a product of the spatial basis matrix Us and the temporal basis sub-matrix Vt(n) of the temporal basis matrix Vt:

$$I = Us \times Vt(n), \tag{3}$$

wherein I refers to the target image.

In some embodiments, the user device 130 may generate the target image by determining a product of the core tensor G, the spatial basis matrix Ux, and the temporal basis sub-matrix $Ut_1(n_1), Ut_2(n_2), \ldots, Ut_N(n_N)$ of each of the N temporal basis matrices $Ut_1, Ut_2, \ldots, Ut_N$.

$$I = G \times_1 Ux \times_2 Ut_1(n_1) \times_3 Ut_2(n_2) \times_4 \ldots \times_{N+1} Ut_N(n_N), \tag{4}$$

wherein $\times_i$ (i=1, 2, 3, ..., N+1) operator refers to the ith mode product.

In 950, the user device 130 (e.g., the second I/O module 810) may display the one or more target images.

In 960, the user device 130 (e.g., the second I/O module 810) may store at least one of the one or more target images in the storage device.

If a user desires to view the plurality of time-series images in the user device 130, it is the spatial basis matrix and the one or more temporal basis matrices, rather than the plurality of time-series images, that are transmitted from the storage device (e.g., the PACS) to the user device 130, which may reduce the transmission pressure. With the spatial basis matrix and the one or more temporal basis matrices, fast reconstruction and display of any one of the plurality of time-series images may be achieved using a device having an ordinary processing capacity (e.g., the user device 130).

In some embodiments, the user device 130 may obtain, from the storage device, the portion of the plurality of time-series images that have been reconstructed (e.g., in operation 630 of the process 600 in FIG. 6) together with the spatial basis matrix and the one or more temporal basis matrices. When receiving an instruction of viewing one of the portion of the plurality of time-series images that have been reconstructed, the user device 130 may directly display the reconstructed image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 960 may be omitted.

In some embodiments, the user may input the instruction of reconstructing one or more target images of the plurality of time-series images through an operation interface of the user device 130. In some embodiments, the user may select and/or input a value of at least one of the plurality parameters through the operation interface to generate the instruction of reconstructing the one or more target images. For example, different values of the plurality of parameters used to scan the ROI of the object to generate the MR data may be provided in the interface as options to be selected. As another example, error messages may be provided in the interface if the user enters an illegal value of a parameter (e.g., a value that does not belong to the values of the plurality of parameters used to scan the ROI of the object to generate the MR data).

Merely by way of example, the user may select a value of the inversion time, a value of the cardiac phase, and a value of the respiratory phase. According to the selected values, the user device 130 may perform operations 930-950 to fast reconstruct an image and display the image in the operation interface.

In some embodiments, firstly, in the values of the plurality of parameters used to scan the ROI of the object to generate the MR data, the user may select at least multiple values of a first parameter of the plurality of parameters and select a value of each of the other of the plurality of parameters through the operation interface to view a dynamic of a dimension of the ROI corresponding to the first parameter. Then, the user device 130 may perform operations 930-950 to fast reconstruct and display the corresponding images in time order, so that the dynamic of the dimension of the ROI corresponding to the first parameter may be presented in the continuously displayed images.

In some embodiments, the user device 130 may simultaneously display two or more interfaces similar to the operation interface described above.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A user device, wherein
    the user device is connected to a first storage device, the first storage device being configured to store a data set determined by a processing device, the first storage device being part of the processing device or connected to the processing device, the data set including a spatial basis and one or more temporal bases, the spatial basis and the one or more temporal bases corresponding to a plurality of time-series images of a region of interest (ROI) of an object, the spatial basis including spatial information of the plurality of time-series images, and the one or more temporal bases including temporal information of the plurality of time-series images; and
    the user device comprises:
        at least one second storage device including a set of instructions; and
        at least one processor in communication with the at least one second storage device, wherein when executing the set of instructions, the at least one processor is directed to cause the user device to perform operations including:
            obtaining, from the first storage device, the data set including the spatial basis and the one or more temporal bases;
            receiving an instruction of reconstructing one or more target images of the plurality of time-series images, the instruction including a value of at least one of a plurality of parameters corresponding to each of the one or more target images;
            for each of the one or more target images, determining one or more temporal basis sub-sets corresponding to the one or more temporal bases based on the value of the at least one of the plurality of parameters corresponding to the target image;
            reconstructing the target image based on the obtained spatial basis and the one or more temporal basis sub-sets; and
            displaying the one or more target images.

2. The user device of claim 1, wherein the at least one parameter relates to at least one of cardiac motion, respiratory motion, or one or more imaging sequence parameters.

3. The user device of claim 1, wherein when executing the set of instructions, the at least one processor is further directed to cause the user device to perform operations including:
    storing at least one of the one or more target images in the first storage device.

4. The user device of claim 1, wherein for each of the one or more target images, the determining one or more temporal basis sub-sets corresponding to the one or more temporal bases includes:
    for each of the one or more target images,
        determining time information corresponding to the target image based on the value of the at least one of the plurality of parameters corresponding to the target image in the instruction; and
        determining the temporal basis sub-set of the each of the one or more temporal basis sub-sets corresponding to the one or more temporal bases based on the time information.

5. The user device of claim 1, wherein the first storage device is a picture archiving and communication system (PACS).

6. The user device of claim 1, wherein the plurality of time-series images includes magnetic resonance (MR) images, computed tomography (CT) images, ultrasound images, or multi-modality images.

7. The user device of claim 1, wherein the spatial basis and the one or more temporal bases relate to a low-rank model that indicates a correlation between the plurality of time-series images.

8. The user device of claim 7, wherein
    the obtained spatial basis includes a spatial basis matrix and the one or more temporal bases include a single temporal basis matrix;
    the spatial basis matrix in combination with the temporal basis matrix represents a low-rank matrix corresponding to a collection of the plurality of time-series images; and
    elements in the spatial basis matrix and the temporal basis matrix are fewer than elements in the low-rank matrix; and
    wherein the reconstructing the target image based on the obtained spatial basis and the one or more temporal basis sub-sets includes:
        reconstructing the target image by determining a product of the spatial basis matrix and the temporal basis sub-set of the single temporal basis matrix.

9. The user device of claim 7, wherein
    the data set further includes a core tensor;
    the obtained spatial basis includes a spatial basis matrix and the one or more temporal bases include two or more temporal basis matrices;
    the spatial basis matrix in combination with the two or more temporal basis matrices and the core tensor represents a low-rank multidimensional tensor corresponding to a collection of the plurality of time-series images; and
    elements in the core tensor, the spatial basis matrix, and the two or more temporal basis matrices are fewer than elements in the low-rank multidimensional tensor; and
    wherein the reconstructing the target image based on the obtained spatial basis and the one or more temporal basis sub-sets includes:
        reconstructing the target image by determining a product of the spatial basis matrix, the two or more temporal basis sub-sets of the two or more temporal basis matrices, and the core tensor.

10. The user device of claim 9, wherein the low-rank multidimensional tensor includes
    a spatial dimension corresponding to the spatial basis matrix, and two or more time dimensions each of which corresponds to one of the two or more temporal basis matrices, respectively.

11. An imaging method implemented on a user device, wherein
the user device is connected to a first storage device, the first storage device being configured to store a data set determined by a processing device, the first storage device being part of the processing device or connected to the processing device, the data set including a spatial basis and one or more temporal bases, the spatial basis and the one or more temporal bases corresponding to a plurality of time-series images of a region of interest (ROI) of an object, the spatial basis including spatial information of the plurality of time-series images, and the one or more temporal bases including temporal information of the plurality of time-series images; and
the method comprises:
obtaining, from the first storage device, the data set including the spatial basis and the one or more temporal bases;
receiving an instruction of reconstructing one or more target images of the plurality of time-series images, the instruction including a value of at least one of a plurality of parameters corresponding to each of the one or more target images;
for each of the one or more target images, determining one or more temporal basis sub-sets corresponding to the one or more temporal bases based on the value of the at least one of the plurality of parameters corresponding to the target image;
reconstructing the target image based on the obtained spatial basis and the one or more temporal basis sub-sets; and
displaying the one or more target images.

12. The method of claim 11, wherein the at least one parameter relates to at least one of cardiac motion, respiratory motion, or one or more imaging sequence parameters.

13. The method of claim 11, further including:
storing at least one of the one or more target images in the first storage device.

14. The method of claim 11, wherein for each of the one or more target images, the determining one or more temporal basis sub-sets corresponding to the one or more temporal bases includes:
for each of the one or more target images,
determining time information corresponding to the target image based on the value of the at least one of the plurality of parameters corresponding to the target image in the instruction; and
determining the temporal basis sub-set of the each of the one or more temporal basis sub-sets corresponding to the one or more temporal bases based on the time information.

15. The method of claim 11, wherein the first storage device is a picture archiving and communication system (PACS).

16. The method of claim 11, wherein the plurality of time-series images includes magnetic resonance (MR) images, computed tomography (CT) images, ultrasound images, or multi-modality images.

17. The method of claim 11, wherein the spatial basis and the one or more temporal bases relate to a low-rank model that indicates a correlation between the plurality of time-series images.

18. The method of claim 17, wherein
the obtained spatial basis includes a spatial basis matrix and the one or more temporal bases include a single temporal basis matrix;
the spatial basis matrix in combination with the temporal basis matrix represents a low-rank matrix corresponding to a collection of the plurality of time-series images; and
elements in the spatial basis matrix and the temporal basis matrix are fewer than elements in the low-rank matrix; and
wherein the reconstructing the target image based on the obtained spatial basis and the one or more temporal basis sub-sets includes:
reconstructing the target image by determining a product of the spatial basis matrix and the temporal basis sub-set of the single temporal basis matrix.

19. The method of claim 17, wherein
the data set further includes a core tensor;
the obtained spatial basis includes a spatial basis matrix and the one or more temporal bases include two or more temporal basis matrices;
the spatial basis matrix in combination with the two or more temporal basis matrices and the core tensor represents a low-rank multidimensional tensor corresponding to a collection of the plurality of time-series images; and
elements in the core tensor, the spatial basis matrix, and the two or more temporal basis matrices are fewer than elements in the low-rank multidimensional tensor; and
wherein the reconstructing the target image based on the obtained spatial basis and the one or more temporal basis sub-sets includes:
reconstructing the target image by determining a product of the spatial basis matrix, the two or more temporal basis sub-sets of the two or more temporal basis matrices, and the core tensor.

20. The method of claim 19, wherein the low-rank multidimensional tensor includes
a spatial dimension corresponding to the spatial basis matrix, and
two or more time dimensions each of which corresponds to one of the two or more temporal basis matrices, respectively.

* * * * *